US010260053B2

(12) United States Patent
Paullin et al.

(10) Patent No.: US 10,260,053 B2
(45) Date of Patent: *Apr. 16, 2019

(54) GLUCOSYLTRANSFERASE ENZYMES FOR PRODUCTION OF GLUCAN POLYMERS

(71) Applicant: E I DU PONT DE NEMOURS AND COMPANY, Wilmington, DE (US)

(72) Inventors: Jayme L. Paullin, Claymont, DE (US); Mark S. Payne, Wilmington, DE (US); T. Joseph Dennes, Parkesburg, PA (US); Yefim Brun, Wilmington, DE (US); Rakesh Nambiar, West Chester, PA (US); Thomas H Scholz, Bear, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,534

(22) Filed: Mar. 23, 2018

(65) Prior Publication Data
US 2018/0273919 A1 Sep. 27, 2018

Related U.S. Application Data

(63) Continuation of application No. 14/619,193, filed on Feb. 11, 2015, now Pat. No. 9,926,541.

(60) Provisional application No. 61/939,811, filed on Feb. 14, 2014.

(51) Int. Cl.
*C12N 9/10* (2006.01)
*C08B 37/00* (2006.01)
*C08B 37/02* (2006.01)
*C12P 19/04* (2006.01)
*C12P 19/18* (2006.01)

(52) U.S. Cl.
CPC ........ *C12N 9/1051* (2013.01); *C08B 37/0009* (2013.01); *C08B 37/0021* (2013.01); *C12P 19/04* (2013.01); *C12P 19/18* (2013.01)

(58) Field of Classification Search
CPC ...... A61K 47/36; C08B 37/0009; C12P 19/04
See application file for complete search history.

*Primary Examiner* — Kagnew H Gebreyesus

(57) ABSTRACT

Compositions are disclosed herein comprising poly alpha-1,3-1,6-glucan with a weight average degree of polymerization ($DP_w$) of at least 1000. This glucan polymer comprises at least 30% alpha-1,3 linkages and at least 30% alpha-1,6 linkages. Further disclosed are glucosyltransferase enzymes that synthesize poly alpha-1,3-1,6-glucan. Ether derivatives of poly alpha-1,3-1,6-glucan and methods of using such derivatives as viscosity modifiers are also disclosed.

17 Claims, No Drawings
Specification includes a Sequence Listing.

GLUCOSYLTRANSFERASE ENZYMES FOR PRODUCTION OF GLUCAN POLYMERS

This application is a continuation of application Ser. No. 14/619,193 (filed Feb. 11, 2015), which claims the benefit of U.S. Provisional Application No. 61/939,811 (filed Feb. 14, 2014). Both of these prior applications are incorporated herein by reference in their entirety.

FIELD OF INVENTION

This invention is in the field of polysaccharides and polysaccharide derivatives. Specifically, this invention pertains to certain poly alpha-1,3-1,6-glucans, glucosyltransferase enzymes that synthesize these glucans, ethers of these glucans, and use of such ethers as viscosity modifiers.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages.

Poly alpha-1,3-glucan has been isolated by contacting an aqueous solution of sucrose with a glucosyltransferase (gtf) enzyme isolated from *Streptococcus salivarius* (Simpson et al., *Microbiology* 141:1451-1460, 1995). U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Development of new glucan polysaccharides and derivatives thereof is desirable given their potential utility in various applications. It is also desirable to identify glucosyltransferase enzymes that can synthesize new glucan polysaccharides, especially those with mixed glycosidic linkages and high molecular weight.

SUMMARY OF INVENTION

In one embodiment, the invention concerns a reaction solution comprising water, sucrose and a glucosyltransferase enzyme that synthesizes poly alpha-1,3-1,6-glucan. The glucosyltransferase enzyme comprises an amino acid sequence that is at least 90% identical to SEQ ID NO:2, SEQ ID NO:4, SEQ ID NO:6, SEQ ID NO:8, or SEQ ID NO:10.

In a second embodiment, (i) at least 30% of the glycosidic linkages of the poly alpha-1,3-1,6-glucan synthesized by the glucosyltransferase enzyme are alpha-1,3 linkages, (ii) at least 30% of the glycosidic linkages of the poly alpha-1,3-1,6-glucan synthesized by the glucosyltransferase enzyme are alpha-1,6 linkages, and (iii) the poly alpha-1,3-1,6-glucan synthesized by the glucosyltransferase enzyme has a weight average degree of polymerization ($DP_w$) of at least 1000.

In a third embodiment, at least 60% of the glycosidic linkages of the poly alpha-1,3-1,6-glucan synthesized by the glucosyltransferase enzyme are alpha-1,6 linkages.

In a fourth embodiment, the $DP_w$ of the poly alpha-1,3-1,6-glucan synthesized by the glucosyltransferase enzyme is at least 10000.

In a fifth embodiment, the glucosyltransferase enzyme comprises the amino acid sequence of SEQ ID NO:2, SEQ ID NO:4, SEQ ID NO:6, SEQ ID NO:8, or SEQ ID NO:10.

In a sixth embodiment, the invention concerns a method for producing poly alpha-1,3-1,6-glucan comprising the step of contacting at least water, sucrose, and a glucosyltransferase enzyme that synthesizes poly alpha-1,3-1,6-glucan. The glucosyltransferase enzyme comprises an amino acid sequence that is at least 90% identical to SEQ ID NO:2, SEQ ID NO:4, SEQ ID NO:6, SEQ ID NO:8, or SEQ ID NO:10. The poly alpha-1,3-1,6-glucan produced in this method can optionally be isolated.

In a seventh embodiment, (i) at least 30% of the glycosidic linkages of the poly alpha-1,3-1,6-glucan synthesized by the glucosyltransferase enzyme in the method are alpha-1,3 linkages, (ii) at least 30% of the glycosidic linkages of the poly alpha-1,3-1,6-glucan are alpha-1,6 linkages, and (iii) the poly alpha-1,3-1,6-glucan has a $DP_w$ of at least 1000.

In an eighth embodiment, at least 60% of the glycosidic linkages of the poly alpha-1,3-1,6-glucan synthesized by the glucosyltransferase enzyme in the method are alpha-1,6 linkages.

In a ninth embodiment, the $DP_w$ of poly alpha-1,3-1,6-glucan synthesized by the glucosyltransferase enzyme in the method is at least 10000.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
| --- | --- | --- |
| "4297 gtf", *Streptococcus oralis*. DNA codon-optimized for expression in *E. coli*. The first 228 amino acids of the protein are deleted compared to GENBANK Identification No. 7684297, which discloses "glucosyltransferase". | 1 | 2 (1348 aa) |
| "3298 gtf", *Streptococcus* sp. C150. The first 209 amino acids of the protein are deleted compared to GENBANK Identification No. 322373298, which discloses "glucosyltransferase-S". | 3 | 4 (1242 aa) |
| "0544 gtf", *Streptococcus mutans*. DNA codon-optimized for expression in *E. coli*. The first 164 amino acids of the protein are deleted compared to GENBANK Identification No. 290580544, which discloses "glucosyltransferase-I". | 5 | 6 (1313 aa) |
| "5618 gtf", *Streptococcus sanguinis*. DNA codon-optimized for expression in *E. coli*. The first 223 amino acids of the protein are deleted compared to GENBANK Identification No. 328945618, which discloses "glucosyltransferase-S". | 7 | 8 (1348 aa) |
| "2379 gtf", *Streptococcus salivarius*. DNA codon-optimized for expression in *E. coli*. The first 203 amino acids of the protein are deleted compared to GENBANK Identification No. 662379, which discloses "glucosyltransferase". | 9 | 10 (1247 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The term "glucan" herein refers to a polysaccharide of D-glucose monomers that are linked by glycosidic linkages.

The terms "glycosidic linkage" and "glycosidic bond" are used interchangeably herein and refer to the type of covalent bond that joins a carbohydrate molecule to another carbohydrate molecule. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the type of covalent bond that joins alpha-D-glucose molecules to each other through carbons 1 and 6 on adjacent alpha-D-glucose rings. Herein, "alpha-D-glucose" will be referred to as "glucose." All glycosidic linkages disclosed herein are alpha-glycosidic linkages, except where otherwise noted.

The glycosidic linkage profile of a poly alpha-1,3-1,6-glucan herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The terms "poly alpha-1,3-1,6-glucan", "alpha-1,3-1,6-glucan polymer", and "poly (alpha-1,3)(alpha-1,6) glucan" are used interchangeably herein (note that the order of the linkage denotations "1,3" and "1,6" in these terms is of no moment). Poly alpha-1,3-1,6-glucan herein is a polymer comprising glucose monomeric units linked together by glycosidic linkages, wherein at least about 30% of the glycosidic linkages are alpha-1,3-glycosidic linkages, and at least about 30% of the glycosidic linkages are alpha-1,6-glycosidic linkages. Poly alpha-1,3-1,6-glucan is a type of polysaccharide containing a mixed glycosidic linkage content. The meaning of the term poly alpha-1,3-1,6-glucan in certain embodiments herein excludes "alternan," which is a glucan containing alpha-1,3 linkages and alpha-1,6 linkages that consecutively alternate with each other (U.S. Pat. No. 5,702,942, U.S. Pat. Appl. Publ. No. 2006/0127328). Alpha-1,3 and alpha-1,6 linkages that "consecutively alternate" with each other can be visually represented by . . . G-1,3-G-1,6-G-1,3-G-1,6-G-1,3-G-1,6-G-1,3-G- . . . , for example, where G represents glucose.

Poly alpha-1,3-1,6-glucan herein, for example, can be produced by a glucosyltransferase enzyme comprising an amino acid sequence that is at least 90% identical to SEQ ID NO:2, SEQ ID NO:4, SEQ ID NO:6, SEQ ID NO:8, or SEQ ID NO:10. Such production can be from a gtf reaction herein.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of a poly alpha-1,3-1,6-glucan or poly alpha-1,3-1,6-glucan ether compound herein can be represented as number-average molecular weight ($M_n$) or as weight-average molecular weight ($M_w$). Alternatively, molecular weight can be represented as Daltons, grams/mole, $DP_w$ (weight average degree of polymerization), or $DP_n$ (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-1,6-glucan and fructose. Other products (byproducts) of a gtf reaction can include glucose (where glucose is hydrolyzed from the glucosyl-gtf enzyme intermediate complex), various soluble oligosaccharides, and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "glucosyltransferase catalytic domain" and "catalytic domain" are used interchangeably herein and refer to the domain of a glucosyltransferase enzyme that provides poly alpha-1,3-1,6-glucan-producing activity to the glucosyltransferase enzyme.

The terms "gtf reaction" and "enzymatic reaction" are used interchangeably herein and refer to a reaction that is performed by a glucosyltransferase enzyme. A "gtf reaction solution" as used herein generally refers to a solution comprising at least one active glucosyltransferase enzyme in a solution comprising sucrose and water, and optionally other components. It is in a gtf reaction solution where the step of contacting water, sucrose and a glucosyltransferase enzyme is performed. The term "under suitable gtf reaction conditions" as used herein, refers to gtf reaction conditions that support conversion of sucrose to poly alpha-1,3-1,6-glucan via glucosyltransferase enzyme activity. A gtf reaction herein is not naturally occurring.

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. "Chimeric gene" refers to any gene that is not a native gene, comprising regulatory and coding sequences that are not found together in nature. A "foreign" or "heterologous" gene refers to a gene that is introduced into the host organism by gene transfer. Foreign genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of particular host cell.

The term "recombinant" or "heterologous" as used herein refers to an artificial combination of two otherwise separate segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used herein refers to the transfer of a nucleic acid molecule into a host organism. The nucleic acid molecule may be a plasmid that replicates autonomously, or it may integrate into the genome of the host organism. Host organisms containing a transformed nucleic acid fragment(s) are "transgenic", "recombinant", or "transformed", and can be referred to as "transformants".

A native amino acid sequence or polynucleotide sequence is naturally occurring, whereas a non-native amino acid sequence or polynucleotide sequence does not occur in nature.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% A identity with a sequence disclosed herein. The variant amino acid sequence or polynucleotide sequence may have the same function/activity of the disclosed sequence, or at least about 85%, 86%, 87%, 88%, 89%, 90%, 91%, 92%, 93%, 94%, 95%, 96%, 97%, 98%, or 99% A of the function/activity of the disclosed sequence.

The term "isolated" as used in certain embodiments refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, an isolated polynucleotide or polypeptide molecule can be comprised within a cell or organism in a heterologous manner. Another example is an isolated glucosyltransferase enzyme.

The terms "poly alpha-1,3-1,6-glucan ether compound", "poly alpha-1,3-1,6-glucan ether", and "poly alpha-1,3-1,6-glucan ether derivative" are used interchangeably herein. A poly alpha-1,3-1,6-glucan ether compound herein is a poly alpha-1,3-1,6-glucan that has been etherified with one or more organic groups such that the compound has a degree of substitution (DoS) with the organic group of about 0.05 to about 3.0. Such etherification occurs at one or more hydroxyl groups of at least 30% of the glucose monomeric units of the poly alpha-1,3-1,6-glucan.

A poly alpha-1,3-1,6-glucan ether compound is termed an "ether" herein by virtue of comprising the substructure —$C_G$—O—C—, where "—$C_G$—" represents a carbon atom of a glucose monomeric unit of a poly alpha-1,3-1,6-glucan ether compound (where such carbon atom was bonded to a hydroxyl group [—OH] in the poly alpha-1,3-1,6-glucan precursor of the ether), and where "—C—" is a carbon atom of the organic group. Thus, for example, with regard to a glucose monomeric unit (G) involved in -1,3-G-1,3- within an ether herein, $C_G$ atoms 2, 4 and/or 6 of the glucose (G) may independently be linked to an OH group or be in ether linkage to an organic group. Similarly, for example, with regard to a glucose monomeric unit (G) involved in -1,3-G-1,6-within an ether herein, $C_G$ atoms 2, 4 and/or 6 of the glucose (G) may independently be linked to an OH group or be in ether linkage to an organic group. Also, for example, with regard to a glucose monomeric unit (G) involved in -1,6-G-1,6- within an ether herein, $C_G$ atoms 2, 3 and/or 4 of the glucose (G) may independently be linked to an OH group or be in ether linkage to an organic group. Similarly, for example, with regard to a glucose monomeric unit (G) involved in -1,6-G-1,3- within an ether herein, $C_G$ atoms 2, 3 and/or 4 of the glucose (G) may independently be linked to an OH group or be in ether linkage to an organic group.

It would be understood that a "glucose" monomeric unit of a poly alpha-1,3-1,6-glucan ether compound herein typically has one or more organic groups in ether linkage. Thus, such a glucose monomeric unit can also be referred to as an etherized glucose monomeric unit.

Poly alpha-1,3-1,6-glucan ether compounds disclosed herein are synthetic, man-made compounds. Likewise, compositions comprising poly alpha-1,3-1,6-glucan (e.g., isolated poly alpha-1,3-1,6-glucan) are synthetic, man-made compounds.

An "organic group" group as used herein refers to a chain of one or more carbons that (i) has the formula —$C_nH_{2n+1}$ (i.e., an alkyl group, which is completely saturated) or (ii) is mostly saturated but has one or more hydrogens substituted with another atom or functional group (i.e., a "substituted alkyl group"). Such substitution may be with one or more hydroxyl groups, oxygen atoms (thereby forming an aldehyde or ketone group), carboxyl groups, or other alkyl groups. Thus, as examples, an organic group herein can be an alkyl group, carboxy alkyl group, or hydroxy alkyl group.

A "carboxy alkyl" group herein refers to a substituted alkyl group in which one or more hydrogen atoms of the alkyl group are substituted with a carboxyl group. A "hydroxy alkyl" group herein refers to a substituted alkyl group in which one or more hydrogen atoms of the alkyl group are substituted with a hydroxyl group.

A "halide" herein refers to a compound comprising one or more halogen atoms (e.g., fluorine, chlorine, bromine, iodine). A halide herein can refer to a compound comprising one or more halide groups such as fluoride, chloride, bromide, or iodide. A halide group may serve as a reactive group of an etherification agent.

The terms "reaction", "reaction composition", and "etherification reaction" are used interchangeably herein and refer to a reaction comprising at least poly alpha-1,3-1,6-glucan and an etherification agent. These components are typically mixed (e.g., resulting in a slurry) and/or dissolved in a solvent (organic and/or aqueous) comprising alkali hydroxide. A reaction is placed under suitable conditions (e.g., time, temperature) for the etherification agent to etherify one or more hydroxyl groups of the glucose units of poly alpha-1,3-1,6-glucan with an organic group, thereby yielding a poly alpha-1,3-1,6-glucan ether compound.

The term "alkaline conditions" herein refers to a solution or mixture pH of at least 11 or 12. Alkaline conditions can be prepared by any means known in the art, such as by dissolving an alkali hydroxide in a solution or mixture.

The terms "etherification agent" and "alkylation agent" are used interchangeably herein. An etherification agent herein refers to an agent that can be used to etherify one or more hydroxyl groups of glucose units of poly alpha-1,3-1,6-glucan with an organic group. An etherification agent thus comprises an organic group.

The term "poly alpha-1,3-1,6-glucan slurry" herein refers to an aqueous mixture comprising the components of a glucosyltransferase enzymatic reaction such as poly alpha-1,3-1,6-glucan, sucrose, one or more glucosyltransferase enzymes, glucose and fructose.

The term "poly alpha-1,3-1,6-glucan wet cake" herein refers to poly alpha-1,3-1,6-glucan that has been separated from a slurry and washed with water or an aqueous solution. Poly alpha-1,3-1,6-glucan is not dried when preparing a wet cake.

The term "degree of substitution" (DoS) as used herein refers to the average number of hydroxyl groups substituted in each monomeric unit (glucose) of a poly alpha-1,3-1,6-glucan ether compound. Since there are at most three hydroxyl groups in a glucose monomeric unit in a poly alpha-1,3-1,6-glucan herein (which is believed to be linear or branched), the degree of substitution in a poly alpha-1,3-1,6-glucan ether compound herein can be no higher than 3.

The term "molar substitution" (M.S.) as used herein refers to the moles of an organic group per monomeric unit of a poly alpha-1,3-1,6-glucan ether compound. Alternatively, M.S. can refer to the average moles of etherification agent used to react with each monomeric unit in poly alpha-1,3-1,6-glucan (M.S. can thus describe the degree of derivatization with an etherification agent). It is noted that the M.S. value for poly alpha-1,3-1,6-glucan may have no upper limit. For example, when an organic group containing a hydroxyl group (e.g., hydroxyethyl or hydroxypropyl) has been etherified to poly alpha-1,3-1,6-glucan, the hydroxyl group of the organic group may undergo further reaction, thereby coupling more of the organic group to the poly alpha-1,3-1,6-glucan.

The term "crosslink" herein refers to a chemical bond, atom, or group of atoms that connects two adjacent atoms in one or more polymer molecules. It should be understood that, in a composition comprising crosslinked poly alpha-1,3-1,6-glucan ether, crosslinks can be between at least two poly alpha-1,3-1,6-glucan ether molecules (i.e., intermolecular crosslinks); there can also be intramolecular crosslinking. A "crosslinking agent" as used herein is an atom or compound that can create crosslinks.

The terms "hydrocolloid" and "hydrogel" are used interchangeably herein. A hydrocolloid refers to a colloid system in which water is the dispersion medium.

A "colloid" herein refers to a substance that is microscopically dispersed throughout another substance. Therefore, a hydrocolloid herein can also refer to a dispersion, mixture, or solution of poly alpha-1,3-1,6-glucan and/or one or more poly alpha-1,3-1,6-glucan ether compounds in water or aqueous solution.

The term "aqueous solution" herein refers to a solution in which the solvent is water. Poly alpha-1,3-1,6-glucan and/or one or more poly alpha-1,3-1,6-glucan ether compounds herein can be dispersed, mixed, and/or dissolved in an aqueous solution. An aqueous solution can serve as the dispersion medium of a hydrocolloid herein.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pas). A centipoise is one one-hundredth of a poise; one poise is equal to 0.100 kg·m$^{-1}$·s$^{-1}$. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of the hydrocolloid or aqueous solution as shear rate increases. The term "shear thickening behavior" as used herein refers to an increase in the viscosity of the hydrocolloid or aqueous solution as shear rate increases. "Shear rate" herein refers to the rate at which a progressive shearing deformation is applied to the hydrocolloid or aqueous solution. A shearing deformation can be applied rotationally.

The term "contacting" as used herein with respect to methods of increasing the viscosity of an aqueous composition refers to any action that results in bringing together an aqueous composition and a poly alpha-1,3-1,6-glucan ether compound. Contacting can be performed by any means known in the art, such as dissolving, mixing, shaking, or homogenization, for example.

Embodiments of the disclosed invention concern a reaction solution comprising water, sucrose, and a glucosyltransferase enzyme that synthesizes poly alpha-1,3-1,6-glucan. The glucosyltransferase enzyme comprises an amino acid sequence that is at least 90% identical to SEQ ID NO:2, SEQ ID NO:4, SEQ ID NO:6, SEQ ID NO:8, or SEQ ID NO:10. Significantly, these enzymes can synthesize poly alpha-1,3-1,6-glucan that can be derivatized into ethers having enhanced viscosity modification qualities.

Regarding poly alpha-1,3-1,6-glucan produced in a reaction solution herein:

(i) at least 30% of the glycosidic linkages of the poly alpha-1,3-1,6-glucan are alpha-1,3 linkages, (ii) at least 30% of the glycosidic linkages of the poly alpha-1,3-1,6-glucan are alpha-1,6 linkages, and (iii) the poly alpha-1,3-1,6-glucan has a weight average degree of polymerization (DP$_w$) of at least 1000.

At least 30% of the glycosidic linkages of poly alpha-1,3-1,6-glucan synthesized by a glucosyltransferase enzyme herein are alpha-1,3 linkages, and at least 30% of the glycosidic linkages are alpha-1,6 linkages. Alternatively, the percentage of alpha-1,3 linkages can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, or 64%. Alternatively still, the percentage of alpha-1,6 linkages can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, or 69%.

A poly alpha-1,3-1,6-glucan synthesized by a glucosyltransferase enzyme herein can have any one the aforementioned percentages of alpha-1,3 linkages and any one of the aforementioned percentages of alpha-1,6 linkages, just so long that the total of the percentages is not greater than 100%. For example, the poly alpha-1,3-1,6-glucan can have (i) any one of 30%, 31%, 32%, 33%, 34%, 35%, 36%, 37%, 38%, 39%, or 40% (30%-40%) alpha-1,3 linkages and (ii) any one of 60%, 61%, 62%, 63%, 64%, 65%, 66%, 67%, 68%, or 69% (60%-69%) alpha-1,6 linkages, just so long that the total of the percentages is not greater than 100%. Non-limiting examples include poly alpha-1,3-1,6-glucan with 31% alpha-1,3 linkages and 67% alpha-1,6 linkages. Other examples of alpha-1,3 and alpha-1,6 linkage profiles are provided in Table 2. In certain embodiments, at least 60% of the glycosidic linkages of poly alpha-1,3-1,6-glucan produced in a gtf reaction solution herein are alpha-1,6 linkages.

Poly alpha-1,3-1,6-glucan synthesized by a glucosyltransferase enzyme herein can have, for example, less than 10%, 9%, 8%, 7%, 6%, 5%, 4%, 3%, 2%, or 1% of glycosidic linkages other than alpha-1,3 and alpha-1,6. In another embodiment, poly alpha-1,3-1,6-glucan only has alpha-1,3 and alpha-1,6 linkages.

The backbone of a poly alpha-1,3-1,6-glucan synthesized by a glucosyltransferase enzyme herein can be linear/unbranched. Alternatively, there can be branches in the poly alpha-1,3-1,6-glucan. A poly alpha-1,3-1,6-glucan in certain embodiments can thus have no branch points or less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% branch points as a percent of the glycosidic linkages in the polymer.

In certain embodiments of the disclosed invention, a glucosyltransferase enzyme can synthesize poly alpha-1,3-1,6-glucan comprising alpha-1,3 linkages and alpha-1,6 linkages that do not consecutively alternate with each other. For the following discussion, consider that . . . G-1,3-G-1,6-G-1,3-G-1,6-G-1,3-G- . . . (where G represents glucose) represents a stretch of six glucose monomeric units linked by consecutively alternating alpha-1,3 linkages and alpha-1,6 linkages. Alternatively, poly alpha-1,3-1,6-glucan synthesized by a glucosyltransferase enzyme herein can comprise, for example, less than 2, 3, 4, 5, 6, 7, 8, 9, 10, or more glucose monomeric units that are linked consecutively with alternating alpha-1,3 and alpha-1,6 linkages.

The molecular weight of poly alpha-1,3-1,6-glucan synthesized by a glucosyltransferase enzyme herein can be measured as DP$_w$ (weight average degree of polymerization) or DP$_n$ (number average degree of polymerization). Alternatively, molecular weight can be measured in Daltons or grams/mole. It may also be useful to refer to the number-average molecular weight (M$_n$) or weight-average molecular weight (M$_w$) of the poly alpha-1,3-1,6-glucan.

Poly alpha-1,3-1,6-glucan synthesized by a glucosyltransferase enzyme herein has a DP$_w$ of at least about 1000. For example, the DP$_w$ of the poly alpha-1,3-1,6-glucan can be at least about 10000. Alternatively, the DP$_w$ can be at least about 1000 to about 15000. Alternatively still, the DP$_w$ can be at least about 1000, 2000, 3000, 4000, 5000, 6000, 7000, 8000, 9000, 10000, 11000, 12000, 13000, 14000, or 15000 (or any integer between 1000 and 15000), for example. Given that poly alpha-1,3-1,6-glucan herein has a DP$_w$ of at least about 1000, such a glucan polymer is typically, but not necessarily, water-insoluble.

In certain embodiments of the disclosed gtf reaction solution, poly alpha-1,3-1,6-glucan can have an M$_w$ of at least about 50000, 100000, 200000, 300000, 400000, 500000, 600000, 700000, 800000, 900000, 1000000, 1100000, 1200000, 1300000, 1400000, 1500000, or 1600000 (or any integer between 50000 and 1600000), for example.

A glucosyltransferase enzyme herein may be obtained from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme herein can comprise, or consist of, an amino acid sequence that is at least 90% identical to SEQ ID NO:2, SEQ ID NO:4, SEQ ID NO:6, SEQ ID NO:8, or SEQ ID NO:10, wherein the glucosyltransferase enzyme has activity. Alternatively, a glucosyltransferase enzyme can comprise, or consist of, an amino acid sequence that is at least 91%, 92%, 93%, 94%, 95%, 96%, 97%, 98%, or 99% identical to SEQ ID NO:4, SEQ ID NO:20, SEQ ID NO:28, or SEQ ID NO:30, wherein the glucosyltransferase enzyme has activity. Alternatively still, a glucosyltransferase enzyme can comprise, or consist of, SEQ ID NO:2, SEQ ID NO:4, SEQ ID NO:6, SEQ ID NO:8, or SEQ ID NO:10.

Given that certain amino acids share similar structural and/or charge features with each other (i.e., conserved), one or more amino acids of the disclosed gtf enzyme sequences may be substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Examples of glucosyltransferase enzymes for use in a gtf reaction solution may be any of the amino acid sequences disclosed herein and that further include 1-300 (or any integer there between) residues on the N-terminus and/or C-terminus. Such additional residues may be from a corresponding wild type sequence from which the glucosyltransferase enzyme is derived, or may be another sequence such as an epitope tag (at either N- or C-terminus) or a heterologous signal peptide (at N-terminus), for example.

The amino acid sequence of a glucosyltransferase enzyme herein can be encoded by the polynucleotide sequence provided in SEQ ID NO:1, SEQ ID NO:3, SEQ ID NO:5, SEQ ID NO:7, or SEQ ID NO:9, for example. Alternatively, such an amino acid sequence can be encoded by a polynucleotide sequence that is at least 90%, 91%, 92%, 93%, 94%, 95%, 96%, 97%, 98%, or 99% identical to SEQ ID NO:1, SEQ ID NO:3, SEQ ID NO:5, SEQ ID NO:7, or SEQ ID NO:9.

One or more different glucosyltransferase enzymes may be used to practice the disclosed invention. The glucosyltransferase enzyme does not have, or has very little (less than 1%), alternansucrase activity, for example.

A glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Oligosaccharides and polysaccharides can serve a primers, for example. Primers that can be used in certain embodiments include dextran and other carbohydrate-based primers, such as hydrolyzed glucan, for example. U.S. Appl. Publ. No. 2013/0244287, which is incorporated herein by reference, discloses preparation of hydrolyzed glucan using poly alpha-1,3-glucan as the starting material. Dextran for use as a primer can be dextran T10 (i.e., dextran having a molecular weight of 10 kD), for example. Alternatively, dextran primer can have a molecular weight of about 2, 4, 6, 8, 10, 12, 14, 16, 18, 20, or 25 kD, for example.

A glucosyltransferase enzyme of the disclosed invention may be produced by any means known in the art. For example, the glucosyltransferase enzyme may be produced recombinantly in a heterologous expression system, such as a microbial heterologous expression system. Examples of heterologous expression systems include bacterial (e.g., *E. coli* such as TOP10 or MG1655; *Bacillus* sp.) and eukaryotic (e.g., yeasts such as *Pichia* sp. and *Saccharomyces* sp.) expression systems.

A glucosyltransferase enzyme described herein may be used in any purification state (e.g., pure or non-pure). For example, the glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v) in a reaction solution for producing poly alpha-1,3-1,6-glucan from sucrose.

A heterologous gene expression system in certain embodiments may be one that is designed for protein secretion. The glucosyltransferase enzyme comprises a signal peptide (signal sequence) in such embodiments. The signal peptide may be either its native signal peptide or a heterologous signal peptide.

The activity of a glucosyltransferase enzyme herein can be determined using any method known in the art. For example, glucosyltransferase enzyme activity can be determined by measuring the production of reducing sugars (fructose and glucose) in a reaction solution containing sucrose (~50 g/L), dextran T10 (~1 mg/mL) and potassium phosphate buffer (~pH 6.5, 50 mM), where the solution is held at ~22-25° C. for ~24-30 hours. The reducing sugars can be measured by adding 0.01 mL of the reaction solution to a mixture containing ~1 N NaOH and ~0.1% triphenyltetrazolium chloride and then monitoring the increase in absorbance at $OD_{480\ nm}$ for ~five minutes.

The temperature of a gtf reaction solution herein can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C.

The temperature of a gtf reaction solution herein may be maintained using various means known in the art. For example, the temperature can be maintained by placing the vessel containing the reaction solution in an air or water bath incubator set at the desired temperature.

The initial concentration of sucrose in a gtf reaction solution herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer between 40 and 160 g/L), for example. "Initial concentration of sucrose" refers to the sucrose concentration in a gtf reaction solution just after all the reaction solution components have been added (water, sucrose, gtf enzyme).

Any grade of sucrose can be used in a reaction solution disclosed herein. For example, the sucrose can be highly pure 99.5%), have a purity of at least 99.0%, or be reagent grade sucrose. Sucrose for use herein may be derived from any renewable sugar source such as sugar cane, sugar beets, cassava, sweet sorghum, or corn. The sucrose can be provided in any form such as crystalline form or non-crystalline form (e.g., syrup or cane juice).

The pH of a gtf reaction solution in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction solution can be from 0 mM to about 100 mM, or about 10, 20, or 50 mM, for example.

The disclosed invention also concerns a method for producing poly alpha-1,3-1,6-glucan comprising the step of contacting at least water, sucrose, and a glucosyltransferase enzyme that synthesizes poly alpha-1,3-1,6-glucan. The glucosyltransferase enzyme comprises an amino acid sequence that is at least 90% identical to SEQ ID NO:2, SEQ ID NO:4, SEQ ID NO:6, SEQ ID NO:8, or SEQ ID NO:10. Poly alpha-1,3-1,6-glucan is produced in the contacting step. This poly alpha-1,3-1,6-glucan can optionally be isolated.

The contacting step in a method herein of producing poly alpha-1,3-1,6-glucan can comprise providing a gtf reaction solution comprising water, sucrose and any glucosyltransferase enzyme disclosed herein. It would be understood that, as the glucosyltransferase enzyme synthesizes poly alpha-1,3-1,6-glucan, the reaction solution typically becomes a reaction mixture given that insoluble poly alpha-1,3-1,6-glucan falls out of solution as indicated by clouding of the reaction. The contacting step of the disclosed method can be performed in any number of ways. For example, the desired amount of sucrose can first be dissolved in water (optionally, other components may also be added at this stage of preparation, such as buffer components), followed by addition of the glucosyltransferase enzyme. The solution may be kept still, or agitated via stirring or orbital shaking, for example. The reaction can be, and typically is, cell-free.

Completion of a gtf reaction in certain embodiments can be determined visually (e.g., no more accumulation of precipitated poly alpha-1,3-1,6-glucan) and/or by measuring the amount of sucrose left in the solution (residual sucrose), where a percent sucrose consumption of over about 90% can indicate reaction completion. Typically, a reaction of the disclosed process can take about 12, 18, 24, 30, 36, 48, 60, 72, 84, or 96 hours to complete. Reaction time may depend, for example, on certain parameters such as the amount of sucrose and glucosyltransferase enzyme used in the reaction.

The yield of poly alpha-1,3-1,6-glucan produced in a gtf reaction in certain embodiments herein can be at least about 4%, 5%, 6%, 7%, or 8%, based on the weight of the sucrose used in the reaction solution.

Poly alpha-1,3-1,6-glucan produced in the disclosed method may optionally be isolated. For example, insoluble poly alpha-1,3-1,6-glucan may be separated by centrifugation or filtration. In doing so, the poly alpha-1,3-1,6-glucan is separated from the rest of the reaction solution, which may comprise water, fructose and certain byproducts (e.g., leucrose, soluble oligosaccharides). This solution may also comprise glucose monomer and residual sucrose.

The linkage profile and/or molecular weight of poly alpha-1,3-1,6-glucan produced in a gtf reaction herein can be any of those disclosed above. For example, (i) at least 30% of the glycosidic linkages are alpha-1,3 linkages, (ii) at least 30% of the glycosidic linkages are alpha-1,6 linkages, and (iii) the poly alpha-1,3-1,6-glucan has a $DP_w$ of at least 1000. Poly alpha-1,3-1,6-glucan produced in a gtf reaction can have at least 60% alpha-1,6 linkages, and/or have a $DP_w$ of at least about 10000.

Embodiments of the disclosed invention concern a composition comprising poly alpha-1,3-1,6-glucan, wherein:

(i) at least 30% of the glycosidic linkages of the poly alpha-1,3-1,6-glucan are alpha-1,3 linkages, (ii) at least 30% of the glycosidic linkages of the poly alpha-1,3-1,6-glucan are alpha-1,6 linkages, (iii) the poly alpha-1,3-1,6-glucan has a weight average degree of polymerization ($DP_w$) of at least 1000; and (iv) the alpha-1,3 linkages and alpha-1,6 linkages of the poly alpha-1,3-1,6-glucan do not consecutively alternate with each other.

Significantly, poly alpha-1,3-1,6-glucan disclosed herein can be derivatized into ethers having enhanced viscosity modification qualities.

At least 30% of the glycosidic linkages of poly alpha-1,3-1,6-glucan disclosed herein are alpha-1,3 linkages, and at least 30% of the glycosidic linkages of the poly alpha-1,3-1,6-glucan are alpha-1,6 linkages. Alternatively, the percentage of alpha-1,3 linkages in poly alpha-1,3-1,6-glucan herein can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, or 64%. Alternatively still, the percentage of alpha-1,6 linkages in poly alpha-1,3-1,6-glucan herein can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, or 69%.

A poly alpha-1,3-1,6-glucan of the invention can have any one the aforementioned percentages of alpha-1,3 linkages and any one of the aforementioned percentages of alpha-1,6 linkages, just so long that the total of the percentages is not greater than 100%. For example, poly alpha-1,3-1,6-glucan herein can have (i) any one of 30%, 31%, 32%, 33%, 34%, 35%, 36%, 37%, 38%, 39%, or 40% (30%-40%) alpha-1,3 linkages and (ii) any one of 60%, 61%, 62%, 63%, 64%, 65%, 66%, 67%, 68%, or 69% (60%-69%) alpha-1,6 linkages, just so long that the total of the percentages is not greater than 100%. Non-limiting examples include poly alpha-1,3-1,6-glucan with 31% alpha-1,3 linkages and 67% alpha-1,6 linkages. Other examples of alpha-1,3 and alpha-1,6 linkage profiles are provided in Table 2. In certain embodiments, at least 60% of the glycosidic linkages of the poly alpha-1,3-1,6-glucan are alpha-1,6 linkages.

A poly alpha-1,3-1,6-glucan of the invention can have, for example, less than 10%, 9%, 8%, 7%, 6%, 5%, 4%, 3%, 2%, or 1% of glycosidic linkages other than alpha-1,3 and alpha-1,6. In another embodiment, a poly alpha-1,3-1,6-glucan only has alpha-1,3 and alpha-1,6 linkages.

The backbone of a poly alpha-1,3-1,6-glucan disclosed herein can be linear/unbranched. Alternatively, there can be branches in the poly alpha-1,3-1,6-glucan. A poly alpha-1,3-1,6-glucan in certain embodiments can thus have no branch points or less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% branch points as a percent of the glycosidic linkages in the polymer.

The alpha-1,3 linkages and alpha-1,6 linkages of a poly alpha-1,3-1,6-glucan in the disclosed composition do not consecutively alternate with each other. For the following discussion, consider that . . . G-1,3-G-1,6-G-1,3-G-1,6-G-1,3-G- . . . (where G represents glucose) represents a stretch of six glucose monomeric units linked by consecutively alternating alpha-1,3 linkages and alpha-1,6 linkages. Poly alpha-1,3-1,6-glucan in certain embodiments herein comprises less than 2, 3, 4, 5, 6, 7, 8, 9, 10, or more glucose monomeric units that are linked consecutively with alternating alpha-1,3 and alpha-1,6 linkages.

The molecular weight of a poly alpha-1,3-1,6-glucan disclosed herein can be measured as $DP_w$ (weight average degree of polymerization) or $DP_n$ (number average degree of polymerization). Alternatively, molecular weight can be measured in Daltons or grams/mole. It may also be useful to refer to the number-average molecular weight ($M_n$) or weight-average molecular weight ($M_w$) of the poly alpha-1,3-1,6-glucan.

A poly alpha-1,3-1,6-glucan herein has a $DP_w$ of at least about 1000. For example, the $DP_w$ of the poly alpha-1,3-1,6-glucan can be at least about 10000. Alternatively, the $DP_w$ can be at least about 1000 to about 15000. Alternatively still, the $DP_w$ can be at least about 1000, 2000, 3000, 4000, 5000, 6000, 7000, 8000, 9000, 10000, 11000, 12000, 13000, 14000, or 15000 (or any integer between 1000 and 15000), for example. Given that a poly alpha-1,3-1,6-glucan herein has a $DP_w$ of at least about 1000, such a glucan polymer is typically, but not necessarily, water-insoluble.

A poly alpha-1,3-1,6-glucan herein can have an $M_w$ of at least about 50000, 100000, 200000, 300000, 400000, 500000, 600000, 700000, 800000, 900000, 1000000, 1100000, 1200000, 1300000, 1400000, 1500000, or 1600000 (or any integer between 50000 and 1600000), for example. The $M_w$ in certain embodiments is at least about 1000000.

A poly alpha-1,3-1,6-glucan herein can comprise at least 6 glucose monomeric units, for example. Alternatively, the number of glucose monomeric units can be at least 10, 50, 100, 500, 1000, 2000, 3000, 4000, 5000, 6000, 7000, 8000, or 9000 (or any integer between 10 and 9000), for example.

Poly alpha-1,3-1,6-glucan herein can be produced, for example, using a glucosyltransferase enzyme comprising an amino acid sequence that is at least 90% identical to SEQ ID NO:2, SEQ ID NO:4, SEQ ID NO:6, SEQ ID NO:8, or SEQ ID NO:10. Alternatively, the glucosyltransferase enzyme can comprise an amino acid sequence that is at least 91%, 92%, 93%, 94%, 95%, 96%, 97%, 98%, or 99% identical to, or 100% identical to, SEQ ID NO:2, SEQ ID NO:4, SEQ ID NO:6, SEQ ID NO:8, or SEQ ID NO:10. Production of poly alpha-1,3-1,6-glucan of the disclosed invention can be accomplished with a gtf reaction as disclosed herein, for example.

Poly alpha-1,3-1,6-glucan herein can be provided in the form of a powder when dry, or a paste, colloid or other dispersion when wet, for example. A composition comprising poly alpha-1,3-1,6-glucan in certain embodiments is one in which the constituent poly alpha-1,3-1,6-glucan behaves as a thickening agent. It is believed that poly alpha-1,3-1,6-glucan herein is suitable as a thickening agent, which is a substance that absorbs liquids such as water and swells upon such absorption. Swelling of poly alpha-1,3-1,6-glucan in a liquid can yield a slurry or colloid, for example.

A composition comprising poly alpha-1,3-1,6-glucan may be in the form of a personal care product, pharmaceutical product, food product, household product, or industrial product, such as any of those products disclosed below for the application of ether derivatives of poly alpha-1,3-1,6-glucan. The amount of poly alpha-1,3-1,6-glucan in the composition can be, for example, about 0.1-10 wt %, 0.1-5 wt %, 0.1-4 wt %, 0.1-3 wt %, 0.1-2 wt %, or 0.1-1 wt %, or an amount that provides the desired degree of thickening to the composition.

Embodiments of the disclosed invention concern a composition comprising a poly alpha-1,3-1,6-glucan ether compound, wherein:

(i) at least 30% of the glycosidic linkages of the poly alpha-1,3-1,6-glucan ether compound are alpha-1,3 linkages, (ii) at least 30% of the glycosidic linkages of the poly alpha-1,3-1,6-glucan ether compound are alpha-1,6 linkages, (iii) the poly alpha-1,3-1,6-glucan ether compound has a weight average degree of polymerization ($DP_w$) of at least 1000;

(iv) the alpha-1,3 linkages and alpha-1,6 linkages of the poly alpha-1,3-1,6-glucan ether compound do not consecutively alternate with each other, and (v) the poly alpha-1,3-1,6-glucan ether compound has a degree of substitution (DoS) with an organic group of about 0.05 to about 3.0.

Significantly, a poly alpha-1,3-1,6-glucan ether compound disclosed herein has enhanced viscosity modification qualities such as the ability to viscosify an aqueous composition at low concentration. Also, a poly alpha-1,3-1,6-glucan ether compound herein can have a relatively low DoS and still be an effective viscosity modifier.

At least 30% of the glycosidic linkages of a poly alpha-1,3-1,6-glucan ether compound disclosed herein are alpha-1,3 linkages, and at least 30% of the glycosidic linkages of the poly alpha-1,3-1,6-glucan ether compound are alpha-1,6 linkages. Alternatively, the percentage of alpha-1,3 linkages in a poly alpha-1,3-1,6-glucan ether compound herein can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, or 64%. Alternatively still, the percentage of alpha-1,6 linkages in a poly alpha-1,3-1,6-glucan ether compound herein can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, or 69%.

A poly alpha-1,3-1,6-glucan ether compound of the invention can have any one the aforementioned percentages of alpha-1,3 linkages and any one of the aforementioned percentages of alpha-1,6 linkages, just so long that the total of the percentages is not greater than 100%. For example, the poly alpha-1,3-1,6-glucan ether compound can have (i) any one of 30%, 31%, 32%, 33%, 34%, 35%, 36%, 37%, 38%, 39%, or 40% (30%-40%) alpha-1,3 linkages and (ii) any one of 60%, 61%, 62%, 63%, 64%, 65%, 66%, 67%, 68%, or 69% (60%-69%) alpha-1,6 linkages, just so long that the total of the percentages is not greater than 100%. Non-limiting examples include poly alpha-1,3-1,6-glucan ether compounds with 31% alpha-1,3 linkages and 67% alpha-1,6 linkages. Other examples of alpha-1,3 and alpha-1,6 linkage profiles of certain poly alpha-1,3-1,6-glucan ether compounds herein are provided in Table 2, which discloses linkage profiles of isolated poly alpha-1,3-1,6-glucan that can be used to prepare the disclosed ethers. In certain embodiments, at least 60% of the glycosidic linkages of the poly alpha-1,3-1,6-glucan ether compound are alpha-1,6 linkages.

A poly alpha-1,3-1,6-glucan ether compound of the invention can have, for example, less than 10%, 9%, 8%, 7%, 6%, 5%, 4%, 3%, 2%, or 1% of glycosidic linkages other than alpha-1,3 and alpha-1,6. In another embodiment, a poly alpha-1,3-1,6-glucan ether compound only has alpha-1,3 and alpha-1,6 linkages.

The backbone of a poly alpha-1,3-1,6-glucan ether compound disclosed herein can be linear/unbranched. Alternatively, there can be branches in the poly alpha-1,3-1,6-glucan ether compound. A poly alpha-1,3-1,6-glucan ether compound in certain embodiments can thus have no branch points or less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% branch points as a percent of the glycosidic linkages in the polymer.

The alpha-1,3 linkages and alpha-1,6 linkages of a poly alpha-1,3-1,6-glucan ether compound disclosed herein do not consecutively alternate with each other. For the following discussion, consider that . . . G-1,3-G-1,6-G-1,3-G-1,6-G-1,3-G- . . . (where G represents etherized glucose) represents a stretch of six glucose monomeric units linked by consecutively alternating alpha-1,3 linkages and alpha-1,6 linkages. Poly alpha-1,3-1,6-glucan ether compounds in certain embodiments herein less than 2, 3, 4, 5, 6, 7, 8, 9, 10, or more glucose monomeric units that are linked consecutively with alternating alpha-1,3 and alpha-1,6 linkages.

The molecular weight of a poly alpha-1,3-1,6-glucan ether compound disclosed herein can be measured as $DP_w$ (weight average degree of polymerization) or $DP_n$ (number average degree of polymerization). Alternatively, molecular weight can be measured in Daltons or grams/mole. It may also be useful to refer to the number-average molecular weight ($M_n$) or weight-average molecular weight ($M_w$) of the poly alpha-1,3-1,6-glucan ether compound.

A poly alpha-1,3-1,6-glucan ether compound herein has a $DP_w$ of at least about 1000. For example, the $DP_w$ of the poly alpha-1,3-1,6-glucan ether compound can be at least about 10000. Alternatively, the $DP_w$ can be at least about 1000 to about 15000. Alternatively still, the $DP_w$ can be at least about 1000, 2000, 3000, 4000, 5000, 6000, 7000, 8000, 9000, 10000, 11000, 12000, 13000, 14000, or 15000 (or any integer between 1000 and 15000), for example.

A poly alpha-1,3-1,6-glucan ether compound herein can have an $M_w$ of at least about 50000, 100000, 200000, 300000, 400000, 500000, 600000, 700000, 800000, 900000, 1000000, 1100000, 1200000, 1300000, 1400000, 1500000, or 1600000 (or any integer between 50000 and 1600000), for example. The $M_w$ in certain embodiments is at least about 1000000.

A poly alpha-1,3-1,6-glucan ether compound herein can comprise at least 6 glucose monomeric units (most of such units typically contain ether-linked organic groups), for example. Alternatively, the number of glucose monomeric units can be at least 10, 50, 100, 500, 1000, 2000, 3000, 4000, 5000, 6000, 7000, 8000, or 9000 (or any integer between 10 and 9000), for example.

Poly alpha-1,3-1,6-glucan ether compounds of the invention have a DoS with an organic group of about 0.05 to about 3.0. In certain embodiments, the DoS of a poly alpha-1,3-1,6-glucan ether compound can be about 0.3 to 1.0. The DoS can alternatively be at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

The percentage of glucose monomeric units of a poly alpha-1,3-1,6-glucan ether compound herein that are ether-linked to an organic group (i.e., where one or more hydroxyl groups of a glucose monomeric unit have been etherified with an organic group) can vary depending on the degree to which a poly alpha-1,3-1,6-glucan is etherified with an organic group in an etherification reaction. This percentage can be at least 30%, 40%, 50%, 60%, 70%, 80%, 90%, or 100% (or any integer value between 30% and 100%), for example.

It would be understood that, depending on the glycosidic linkages with which a glucose monomeric unit of an ether compound is involved (e.g., -1,6-G-1,3-), certain carbon atoms of the glucose monomeric unit may independently be linked to an OH group or be in ether linkage to an organic group.

An organic group herein may be an alkyl group such as a methyl, ethyl, propyl, butyl, pentyl, hexyl, heptyl, octyl, nonyl, or decyl group, for example.

Alternatively, an organic group may be a substituted alkyl group in which there is a substitution on one or more carbons of the alkyl group. The substitution(s) may be one or more hydroxyl, aldehyde, ketone, and/or carboxyl groups. For example, a substituted alkyl group may be a hydroxy alkyl group, dihydroxy alkyl group, or carboxy alkyl group.

Examples of suitable hydroxy alkyl groups are hydroxymethyl (—CH$_2$OH), hydroxyethyl (e.g., —CH$_2$CH$_2$OH, —CH(OH)CH$_3$), hydroxypropyl (e.g., —CH$_2$CH$_2$CH$_2$OH, —CH$_2$CH(OH)CH$_3$, —CH(OH)CH$_2$CH$_3$), hydroxybutyl and hydroxypentyl groups. Other examples include dihydroxy alkyl groups (diols) such as dihydroxymethyl, dihydroxyethyl (e.g., —CH(OH)CH$_2$OH), dihydroxypropyl (e.g., —CH$_2$CH(OH)CH$_2$OH, —CH(OH)CH(OH)CH$_3$), dihydroxybutyl and dihydroxypentyl groups.

Examples of suitable carboxy alkyl groups are carboxymethyl (—CH$_2$COOH), carboxyethyl (e.g., —CH$_2$CH$_2$COOH, —CH(COOH)CH$_3$), carboxypropyl (e.g., —CH$_2$CH$_2$CH$_2$COOH, —CH$_2$CH(COOH)CH$_3$, —CH(COOH)CH$_2$CH$_3$), carboxybutyl and carboxypentyl groups.

Alternatively still, one or more carbons of an alkyl group can have a substitution(s) with another alkyl group. Examples of such substituent alkyl groups are methyl, ethyl and propyl groups. To illustrate, an organic group can be —CH(CH$_3$)CH$_2$CH$_3$ or —CH$_2$CH(CH$_3$)CH$_3$, for example, which are both propyl groups having a methyl substitution.

As should be clear from the above examples of various substituted alkyl groups, a substitution (e.g., hydroxy or carboxy group) on an alkyl group in certain embodiments may be bonded to the terminal carbon atom of the alkyl group, where the terminal carbon group is opposite the terminus that is in ether linkage to a glucose monomeric unit in a poly alpha-1,3-1,6-glucan ether compound. An example of this terminal substitution is the hydroxypropyl group —CH$_2$CH$_2$CH$_2$OH. Alternatively, a substitution may be on an internal carbon atom of an alkyl group. An example on an internal substitution is the hydroxypropyl group —CH$_2$CH(OH)CH$_3$. An alkyl group can have one or more substitutions, which may be the same (e.g., two hydroxyl groups [dihydroxy]) or different (e.g., a hydroxyl group and a carboxyl group).

Poly alpha-1,3-1,6-glucan ether compounds in certain embodiments disclosed herein may contain one type of organic group. Examples of such compounds contain a carboxy alkyl group as the organic group (carboxyalkyl poly alpha-1,3-1,6-glucan, generically speaking). A specific non-limiting example of such a compound is carboxymethyl poly alpha-1,3-1,6-glucan.

Alternatively, poly alpha-1,3-1,6-glucan ether compounds disclosed herein can contain two or more different types of organic groups. Examples of such compounds contain (i) two different alkyl groups as organic groups, (ii) an alkyl group and a hydroxy alkyl group as organic groups (alkyl hydroxyalkyl poly alpha-1,3-1,6-glucan, generically speaking), (iii) an alkyl group and a carboxy alkyl group as organic groups (alkyl carboxyalkyl poly alpha-1,3-1,6-glucan, generically speaking), (iv) a hydroxy alkyl group and a carboxy alkyl group as organic groups (hydroxyalkyl carboxyalkyl poly alpha-1,3-1,6-glucan, generically speaking), (v) two different hydroxy alkyl groups as organic groups, or (vi) two different carboxy alkyl groups as organic groups. Specific non-limiting examples of such compounds include ethyl hydroxyethyl poly alpha-1,3-1,6-glucan, hydroxyalkyl methyl poly alpha-1,3-1,6-glucan, carboxymethyl hydroxyethyl poly alpha-1,3-1,6-glucan, and carboxymethyl hydroxypropyl poly alpha-1,3-1,6-glucan.

Poly alpha-1,3-1,6-glucan ether compounds may be derived from any poly alpha-1,3-1,6-glucan disclosed herein. For example, a poly alpha-1,3-1,6-glucan ether compound of the invention can be produced by ether-derivatizing poly alpha-1,3-1,6-glucan using an etherification reaction as disclosed herein.

In certain embodiments of the disclosed invention, the poly alpha-1,3-1,6-glucan from which a poly alpha-1,3-1,6-glucan ether compound is derived is a product of a glucosyltransferase enzyme comprising an amino acid sequence that is at least 90% identical to SEQ ID NO:2, SEQ ID NO:4, SEQ ID NO:6, SEQ ID NO:8, or SEQ ID NO:10. Alternatively, the glucosyltransferase enzyme can comprise an amino acid sequence that is at least 91%, 92%, 93%, 94%, 95%, 96%, 97%, 98%, or 99% identical to, or 100% identical to, SEQ ID NO:2, SEQ ID NO:4, SEQ ID NO:6, SEQ ID NO:8, or SEQ ID NO:10.

In certain embodiments of the disclosed invention, a composition comprising a poly alpha-1,3-1,6-glucan ether compound can be a hydrocolloid or aqueous solution having a viscosity of at least about 10 cPs. Alternatively, such a hydrocolloid or aqueous solution has a viscosity of at least about 100, 250, 500, 750, 1000, 1250, 1500, 1750, 2000, 2250, 2500, 3000, 3500, or 4000 cPs (or any integer between 100 and 4000 cPs), for example.

Viscosity can be measured with the hydrocolloid or aqueous solution at any temperature between about 3° C. to about 110° C. (or any integer between 3 and 110° C.). Alternatively, viscosity can be measured at a temperature between about 4° C. to 30° C., or about 20° C. to 25° C. Viscosity can be measured at atmospheric pressure (about 760 torr) or any other higher or lower pressure.

The viscosity of a hydrocolloid or aqueous solution disclosed herein can be measured using a viscometer or rheometer, or using any other means known in the art. It would be understood by those skilled in the art that a viscometer or rheometer can be used to measure the viscosity of those hydrocolloids and aqueous solutions of the invention that exhibit shear thinning behavior or shear thickening behavior (i.e., liquids with viscosities that vary with flow conditions). The viscosity of such embodiments can be measured at a rotational shear rate of about 10 to 1000 rpm (revolutions per minute) (or any integer between 10 and 1000 rpm), for example. Alternatively, viscosity can be measured at a rotational shear rate of about 10, 60, 150, 250, or 600 rpm.

The pH of a hydrocolloid or aqueous solution disclosed herein can be between about 2.0 to about 12.0. Alternatively, pH can be about 2.0, 3.0, 4.0, 5.0, 6.0, 7.0, 8.0, 9.0, 10.0, 11.0, 12.0; between about 4.0 and 8.0; or between about 5.0 and 8.0.

A poly alpha-1,3-1,6-glucan ether compound disclosed herein can be present in a hydrocolloid or aqueous solution at a weight percentage (wt %) of at least about 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, for example.

A hydrocolloid or aqueous solution herein can comprise other components in addition to a poly alpha-1,3-1,6-glucan ether compound. For example, the hydrocolloid or aqueous solution can comprise one or more salts such as a sodium salt (e.g., NaCl, Na$_2$SO$_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a hydrocolloid or aqueous solution, for example. A salt can be present in a hydrocolloid or aqueous solution at a wt % of about 0.01% to about 10.00% (or any hundredth increment between 0.01 and 10.00).

Those skilled in the art would understand that in certain embodiments of the invention, a poly alpha-1,3-1,6-glucan ether compound can be in an anionic form in the hydrocolloid or aqueous solution. Examples may include those poly alpha-1,3-1,6-glucan ether compounds having an organic group comprising an alkyl group substituted with a carboxyl group. Carboxyl (COOH) groups in a carboxyalkyl poly alpha-1,3-1,6-glucan ether compound can convert to carboxylate (COO$^-$) groups in aqueous conditions. Such anionic groups can interact with salt cations such as any of those listed above in (i) (e.g., potassium, sodium, or lithium cation). Thus, a poly alpha-1,3-1,6-glucan ether compound can be a sodium carboxyalkyl poly alpha-1,3-1,6-glucan ether (e.g., sodium carboxymethyl poly alpha-1,3-1,6-glucan), potassium carboxyalkyl poly alpha-1,3-1,6-glucan ether (e.g., potassium carboxymethyl poly alpha-1,3-1,6-glucan), or lithium carboxyalkyl poly alpha-1,3-1,6-glucan ether (e.g., lithium carboxymethyl poly alpha-1,3-1,6-glucan), for example.

A poly alpha-1,3-1,6-glucan ether compound disclosed herein may be crosslinked using any means known in the art. Such crosslinks may be borate crosslinks, where the borate is from any boron-containing compound (e.g., boric acid, diborates, tetraborates, pentaborates, polymeric compounds such as Polybor®, polymeric compounds of boric acid, alkali borates). Alternatively, crosslinks can be provided with polyvalent metals such as titanium or zirconium. Titanium crosslinks may be provided using titanium IV-containing compounds such as titanium ammonium lactate, titanium triethanolamine, titanium acetylacetonate, and polyhydroxy complexes of titanium. Zirconium crosslinks can be provided using zirconium IV-containing compounds such as zirconium lactate, zirconium carbonate, zirconium acetylacetonate, zirconium triethanolamine, zirconium diisopropylamine lactate and polyhydroxy complexes of zirconium. Alternatively still, crosslinks can be provided with any crosslinking agent described in U.S. Pat. Nos. 4,462,917; 4,464,270; 4,477,360 and 4,799,550; which are all incorporated herein by reference. A crosslinking agent (e.g., borate) may be present in a hydrocolloid or aqueous solution at a concentration of about 0.2% to 20 wt %, or about 0.1, 0.2, 0.3, 0.4, 0.5, 1, 2, 3, 4, 5, 6, 7, 8, 9, 10, 15, or 20 wt %, for example.

It is believed that a poly alpha-1,3-1,6-glucan ether compound disclosed herein that is crosslinked typically has a higher viscosity in an aqueous solution compared to its non-crosslinked counterpart. In addition, it is believed that a crosslinked poly alpha-1,3-1,6-glucan ether compound can have increased shear thickening behavior compared to its non-crosslinked counterpart.

Hydrocolloids and aqueous solutions in certain embodiments of the invention are believed to have either shear thinning behavior or shear thickening behavior. Shear thinning behavior is observed as a decrease in viscosity of the hydrocolloid or aqueous solution as shear rate increases, whereas shear thickening behavior is observed as an increase in viscosity of the hydrocolloid or aqueous solution as shear rate increases. Modification of the shear thinning behavior or shear thickening behavior of an aqueous solution herein is due to the admixture of a poly alpha-1,3-1,6-glucan ether to the aqueous composition. Thus, one or more poly alpha-1,3-1,6-glucan ether compounds of the invention can be added to an aqueous liquid, solution, or mixture to modify its rheological profile (i.e., the flow properties of the aqueous liquid, solution, or mixture are modified). Also, one or more poly alpha-1,3-1,6-glucan ether compounds of the invention can be added to an aqueous liquid, solution, or mixture to modify its viscosity.

The rheological properties of hydrocolloids and aqueous solutions of the invention can be observed by measuring viscosity over an increasing rotational shear rate (e.g., from about 10 rpm to about 250 rpm). For example, shear thinning behavior of a hydrocolloid or aqueous solution disclosed herein can be observed as a decrease in viscosity (cPs) by at least about 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of a hydrocolloid or aqueous solution disclosed herein can be observed as an increase in viscosity (cPs) by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

A hydrocolloid or aqueous solution disclosed herein can be in the form of, and/or comprised in, a personal care product, pharmaceutical product, food product, household product, or industrial product. Poly alpha-1,3-1,6-glucan ether compounds disclosed herein can be used as thickening agents in each of these products. Such a thickening agent may be used in conjunction with one or more other types of thickening agents if desired, such as those disclosed in U.S. Pat. No. 8,541,041, the disclosure of which is incorporated herein by reference in its entirety.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient. An active ingredient is generally recognized as an ingredient that causes the intended pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup or other product including, but not limited to, a lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, preshaving product, after-shaving product, cleanser, skin gel, rinse, toothpaste, or mouthwash, for example.

A pharmaceutical product herein can be in the form of an emulsion, liquid, elixir, gel, suspension, solution, cream, or ointment, for example. Also, a pharmaceutical product herein can be in the form of any of the personal care products disclosed herein. A pharmaceutical product can further comprise one or more pharmaceutically acceptable carriers, diluents, and/or pharmaceutically acceptable salts. A poly alpha-1,3-1,6-glucan ether compound disclosed herein can also be used in capsules, encapsulants, tablet coatings, and as an excipients for medicaments and drugs.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; beverages; frozen desserts; ice cream; cultured dairy products such as cottage cheese, yogurt, cheeses, and sour creams; cake icing and glazes; whipped topping; leavened and unleavened baked goods; and the like.

Poly alpha-1,3-1,6-glucan ether compounds, hydrocolloids and aqueous compositions disclosed herein can be used to provide one or more of the following physical properties to a food product (or any personal care product, pharmaceutical product, or industrial product): thickening, freeze/thaw stability, lubricity, moisture retention and release, film formation, texture, consistency, shape retention, emulsification, binding, suspension, and gelation, for example. Poly alpha-1,3-1,6-glucan ether compounds disclosed herein can typically be used in a food product at a level of about 0.01 to about 5 wt %, for example.

A poly alpha-1,3-1,6-glucan ether compound disclosed herein can be comprised in a foodstuff or any other ingestible material (e.g., enteral pharmaceutical preparation) in an amount that provides the desired degree of thickening. For example, the concentration or amount of a poly alpha-1,3-1,6-glucan ether compound in a product, on a weight basis, can be about 0.1-3 wt %, 0.1-4 wt %, 0.1-5 wt %, or 0.1-10 wt %.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, and injection molding and ceramics; spray adherents and suspending/dispersing aids for pesticides, herbicides, and fertilizers; fabric softeners; laundry detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; emulsion-based metal cleaning fluids used in electroplating, phosphatizing, galvanizing and/or general metal cleaning operations; hydraulic fluids (e.g., those used for fracking in downhole operations); and aqueous mineral slurries, for example.

The disclosed invention also concerns a method for increasing the viscosity of an aqueous composition. This method comprises contacting one or more poly alpha-1,3-1,6-glucan ether compounds with the aqueous composition, wherein:

(i) at least 30% of the glycosidic linkages of the poly alpha-1,3-1,6-glucan ether compound are alpha-1,3 linkages, (ii) at least 30% of the glycosidic linkages of the poly alpha-1,3-1,6-glucan ether compound are alpha-1,6 linkages, (iii) the poly alpha-1,3-1,6-glucan ether compound has a weight average degree of polymerization ($DP_w$) of at least 1000; and (iv) the alpha-1,3 linkages and alpha-1,6 linkages of the poly alpha-1,3-1,6-glucan ether compound do not consecutively alternate with each other.

The contacting step in this method results in increasing the viscosity of the aqueous composition. Any hydrocolloid and aqueous solution disclosed herein can be produced using this method.

An aqueous composition herein can be water (e.g., de-ionized water), an aqueous solution, or a hydrocolloid, for example. The viscosity of an aqueous composition before the contacting step, measured at about 20-25° C., can be about 0-10000 cPs (or any integer between 0-10000 cPs). Since the aqueous composition can be a hydrocolloid or the like in certain embodiments, it should be apparent that the method can be used to increase the viscosity of aqueous compositions that are already viscous.

Contacting a poly alpha-1,3-1,6-glucan ether compound(s) disclosed herein with an aqueous composition increases the viscosity of the aqueous composition. The increase in viscosity can be an increase of at least about 1%, 10%, 100%, 1000%, 100000%, or 1000000% (or any integer between 1% and 1000000%), for example, compared to the viscosity of the aqueous composition before the mixing or dissolving step. It should be apparent that very large percent increases in viscosity can be obtained with the disclosed method when the aqueous composition has little to no viscosity before the contacting step.

The contacting step in a method for increasing the viscosity of an aqueous composition can be performed by mixing or dissolving any poly alpha-1,3-1,6-glucan ether compound(s) disclosed herein in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix a poly alpha-1,3-1,6-glucan ether compound with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm). Hydrocolloids and aqueous solutions disclosed herein prepared using a homogenization step can be termed as homogenized hydrocolloids and aqueous solutions.

After a poly alpha-1,3-1,6-glucan ether compound is mixed with or dissolved into the aqueous composition, the resulting aqueous composition may be filtered, or may not be filtered. For example, an aqueous composition prepared with a homogenization step may or may not be filtered.

The disclosed invention also concerns a method for producing a poly alpha-1,3-1,6-glucan ether compound. This method comprises: contacting poly alpha-1,3-1,6-glucan in a reaction under alkaline conditions with at least one etherification agent comprising an organic group, wherein the organic group is etherified to the poly alpha-1,3-1,6-glucan thereby producing a poly alpha-1,3-1,6-glucan ether compound. Further regarding this method:

(i) at least 30% of the glycosidic linkages of the poly alpha-1,3-1,6-glucan are alpha-1,3 linkages, (ii) at least 30% of the glycosidic linkages of the poly alpha-1,3-1,6-glucan are alpha-1,6 linkages, (iii) the poly alpha-1,3-1,6-glucan has a weight average degree of polymerization ($DP_w$) of at least 1000, (iv) the alpha-1,3 linkages and alpha-1,6 linkages of the poly alpha-1,3-1,6-glucan do not consecutively alternate with each other, and (v) the poly alpha-1,3-1,6-glucan ether compound has a degree of substitution (DoS) with the organic group of about 0.05 to about 3.0.

A poly alpha-1,3-1,6-glucan ether compound produced by this method can optionally be isolated.

Poly alpha-1,3-1,6-glucan is contacted in a reaction under alkaline conditions with at least one etherification agent comprising an organic group. This step can be performed, for example, by first preparing alkaline conditions by contacting poly alpha-1,3-1,6-glucan with a solvent and one or more alkali hydroxides to provide a mixture (e.g., slurry) or solution. The alkaline conditions of the etherification reaction can thus comprise an alkali hydroxide solution. The pH of the alkaline conditions can be at least about 11.0, 11.2, 11.4, 11.6, 11.8, 12.0, 12.2, 12.4, 12.6, 12.8, or 13.0.

Various alkali hydroxides can be used, such as sodium hydroxide, potassium hydroxide, calcium hydroxide, lithium hydroxide, and/or tetraethylammonium hydroxide. The concentration of alkali hydroxide in a preparation with poly alpha-1,3-1,6-glucan and a solvent can be from about 1-70 wt %, 5-50 wt %, 5-10 wt %, 10-50 wt %, 10-40 wt %, or 10-30 wt % (or any integer between 1 and 70 wt %). Alternatively, the concentration of alkali hydroxide such as sodium hydroxide can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. An alkali hydroxide used to prepare alkaline conditions may be in a completely aqueous solution or an aqueous solution comprising one or more water-soluble organic solvents such as ethanol or isopropanol. Alternatively, an alkali hydroxide can be added as a solid to provide alkaline conditions.

Various organic solvents that can optionally be included or used as the main solvent when preparing the etherification reaction include alcohols, acetone, dioxane, isopropanol and toluene, for example; none of these solvents dissolve poly alpha-1,3-1,6-glucan. Toluene or isopropanol can be used in certain embodiments. An organic solvent can be added before or after addition of alkali hydroxide. The concentration of an organic solvent (e.g., isopropanol or toluene) in a preparation comprising poly alpha-1,3-1,6-glucan and an alkali hydroxide can be at least about 10, 15, 20, 25, 30, 35, 40, 45, 50, 55, 60, 65, 70, 75, 80, 85, or 90 wt % (or any integer between 10 and 90 wt %).

Alternatively, solvents that can dissolve poly alpha-1,3-1,6-glucan can be used when preparing the etherification reaction. These solvents include, but are not limited to, lithium chloride (LiCl)/N,N-dimethyl-acetamide (DMAc), $SO_2$/diethylamine (DEA)/dimethyl sulfoxide (DMSO), LiCl/1,3-dimethy-2-imidazolidinone (DMI), N,N-dimethylformamide (DMF)/$N_2O_4$, DMSO/tetrabutyl-ammonium fluoride trihydrate (TBAF), N-methylmorpholine-N-oxide (NMMO), Ni(tren)(OH)$_2$ [tren¼tris(2-aminoethyl)amine] aqueous solutions and melts of LiClO$_4$.3H$_2$O, NaOH/urea aqueous solutions, aqueous sodium hydroxide, aqueous potassium hydroxide, formic acid, and ionic liquids.

Poly alpha-1,3-1,6-glucan can be contacted with a solvent and one or more alkali hydroxides by mixing. Such mixing can be performed during or after adding these components with each other. Mixing can be performed by manual mixing, mixing using an overhead mixer, using a magnetic stir bar, or shaking, for example. In certain embodiments, poly alpha-1,3-1,6-glucan can first be mixed in water or an aqueous solution before it is mixed with a solvent and/or alkali hydroxide.

After contacting poly alpha-1,3-1,6-glucan, solvent, and one or more alkali hydroxides with each other, the resulting composition can optionally be maintained at ambient temperature for up to 14 days. The term "ambient temperature" as used herein refers to a temperature between about 15-30° C. or 20-25° C. (or any integer between 15 and 30° C.). Alternatively, the composition can be heated with or without reflux at a temperature from about 30° C. to about 150° C. (or any integer between 30 and 150° C.) for up to about 48 hours. The composition in certain embodiments can be heated at about 55° C. for about 30 minutes or about 60 minutes. Thus, a composition obtained from mixing a poly alpha-1,3-1,6-glucan, solvent, and one or more alkali hydroxides with each other can be heated at about 50, 51, 52, 53, 54, 55, 56, 57, 58, 59, or 60° C. for about 30-90 minutes.

After contacting poly alpha-1,3-1,6-glucan, solvent, and one or more alkali hydroxides with each other, the resulting composition can optionally be filtered (with or without applying a temperature treatment step). Such filtration can be performed using a funnel, centrifuge, press filter, or any other method and/or equipment known in the art that allows removal of liquids from solids. Though filtration would remove much of the alkali hydroxide, the filtered poly alpha-1,3-1,6-glucan would remain alkaline (i.e., mercerized poly alpha-1,3-1,6-glucan), thereby providing alkaline conditions.

An etherification agent comprising an organic group is contacted with poly alpha-1,3-1,6-glucan in a reaction under alkaline conditions in a method herein of producing poly alpha-1,3-1,6-glucan ether compounds. For example, an etherification agent can be added to a composition prepared by contacting poly alpha-1,3-1,6-glucan, solvent, and one or more alkali hydroxides with each other as described above. Alternatively, an etherification agent can be included when preparing the alkaline conditions (e.g., an etherification agent can be mixed with poly alpha-1,3-1,6-glucan and solvent before mixing with alkali hydroxide).

An etherification agent herein refers to an agent that can be used to etherify one or more hydroxyl groups of glucose monomeric units of poly alpha-1,3-1,6-glucan with an organic group as disclosed herein. Examples of such organic groups include alkyl groups, hydroxy alkyl groups, and carboxy alkyl groups. One or more etherification agents may be used in the reaction.

Etherification agents suitable for preparing an alkyl poly alpha-1,3-1,6-glucan ether compound include, for example, dialkyl sulfates, dialkyl carbonates, alkyl halides (e.g., alkyl chloride), iodoalkanes, alkyl triflates (alkyl trifluoromethanesulfonates) and alkyl fluorosulfonates. Thus, examples of etherification agents for producing methyl poly alpha-1,3-1,6-glucan ethers include dimethyl sulfate, dimethyl carbonate, methyl chloride, iodomethane, methyl triflate and methyl fluorosulfonate. Examples of etherification agents for producing ethyl poly alpha-1,3-1,6-glucan ethers include diethyl sulfate, diethyl carbonate, ethyl chloride, iodoethane, ethyl triflate and ethyl fluorosulfonate. Examples of etherification agents for producing propyl poly alpha-1,3-1,6-glucan ethers include dipropyl sulfate, dipropyl carbonate, propyl chloride, iodopropane, propyl triflate and propyl fluorosulfonate. Examples of etherification agents for producing butyl poly alpha-1,3-1,6-glucan ethers include dibutyl sulfate, dibutyl carbonate, butyl chloride, iodobutane and butyl triflate.

Etherification agents suitable for preparing a hydroxyalkyl poly alpha-1,3-1,6-glucan ether compound include, for example, alkylene oxides such as ethylene oxide, propylene oxide (e.g., 1,2-propylene oxide), butylene oxide (e.g., 1,2- butylene oxide; 2,3-butylene oxide; 1,4-butylene oxide), or combinations thereof. As examples, propylene oxide can be used as an etherification agent for preparing hydroxypropyl poly alpha-1,3-1,6-glucan, and ethylene oxide can be used as an etherification agent for preparing hydroxyethyl poly alpha-1,3-1,6-glucan. Alternatively, hydroxyalkyl halides (e.g., hydroxyalkyl chloride) can be used as etherification agents for preparing hydroxyalkyl poly alpha-1,3-1,6-glucan. Examples of hydroxyalkyl halides include hydroxyethyl halide, hydroxypropyl halide (e.g., 2-hydroxypropyl chloride, 3-hydroxypropyl chloride) and hydroxybutyl halide. Alternatively, alkylene chlorohydrins can be used as etherification agents for preparing hydroxyalkyl poly alpha-1,3-1,6-glucan. Alkylene chlorohydrins that can be used include, but are not limited to, ethylene chlorohydrin, propylene chlorohydrin, butylene chlorohydrin, or combinations of these.

Etherification agents suitable for preparing a dihydroxyalkyl poly alpha-1,3-1,6-glucan ether compound include dihydroxyalkyl halides (e.g., dihydroxyalkyl chloride) such as dihydroxyethyl halide, dihydroxypropyl halide (e.g., 2,3-dihydroxypropyl chloride [i.e., 3-chloro-1,2-propanediol]), or dihydroxybutyl halide, for example. 2,3-dihydroxypropyl chloride can be used to prepare dihydroxypropyl poly alpha-1,3-1,6-glucan, for example.

Etherification agents suitable for preparing a carboxyalkyl poly alpha-1,3-1,6-glucan ether compound may include haloalkylates (e.g., chloroalkylate). Examples of haloalkylates include haloacetate (e.g., chloroacetate), 3-halopropionate (e.g., 3-chloropropionate) and 4-halobutyrate (e.g., 4-chlorobutyrate). For example, chloroacetate (monochloroacetate) (e.g., sodium chloroacetate) can be used as an etherification agent to prepare carboxymethyl poly alpha-1,3-1,6-glucan.

When producing a poly alpha-1,3-1,6-glucan ether compound with two or more different organic groups, two or more different etherification agents would be used, accordingly. For example, both an alkylene oxide and an alkyl chloride could be used as etherification agents to produce an alkyl hydroxyalkyl poly alpha-1,3-1,6-glucan ether. Any of the etherification agents disclosed herein may therefore be combined to produce poly alpha-1,3-1,6-glucan ether compounds with two or more different organic groups. Such two or more etherification agents may be used in the reaction at the same time, or may be used sequentially in the reaction. When used sequentially, any of the temperature-treatment (e.g., heating) steps disclosed below may optionally be used between each addition. One may choose sequential introduction of etherification agents in order to control the desired DoS of each organic group. In general, a particular etherification agent would be used first if the organic group it forms in the ether product is desired at a higher DoS compared to the DoS of another organic group to be added.

The amount of etherification agent to be contacted with poly alpha-1,3-1,6-glucan in a reaction under alkaline conditions can be determined based on the DoS required in the poly alpha-1,3-1,6-glucan ether compound being produced. The amount of ether substitution groups on each glucose monomeric unit in poly alpha-1,3-1,6-glucan ether compounds produced herein can be determined using nuclear magnetic resonance (NMR) spectroscopy. The molar substitution (MS) value for poly alpha-1,3-1,6-glucan has no upper limit. In general, an etherification agent can be used in a quantity of at least about 0.05 mole per mole of poly alpha-1,3-1,6-glucan. There is no upper limit to the quantity of etherification agent that can be used.

Reactions for producing poly alpha-1,3-1,6-glucan ether compounds herein can optionally be carried out in a pressure vessel such as a Parr reactor, an autoclave, a shaker tube or any other pressure vessel well known in the art.

A reaction herein can optionally be heated following the step of contacting poly alpha-1,3-1,6-glucan with an etherification agent under alkaline conditions. The reaction temperatures and time of applying such temperatures can be varied within wide limits. For example, a reaction can optionally be maintained at ambient temperature for up to 14 days. Alternatively, a reaction can be heated, with or without reflux, between about 25° C. to about 200° C. (or any integer between 25 and 200° C.). Reaction time can be varied correspondingly: more time at a low temperature and less time at a high temperature.

In certain embodiments of producing carboxymethyl poly alpha-1,3-1,6-glucan, a reaction can be heated to about 55° C. for about 3 hours. Thus, a reaction for preparing a carboxyalkyl poly alpha-1,3-1,6-glucan herein can be heated to about 50° C. to about 60° C. (or any integer between 50 and 60° C.) for about 2 hours to about 5 hours, for example. Etherification agents such as a haloacetate (e.g., monochloroacetate) may be used in these embodiments, for example.

Optionally, an etherification reaction herein can be maintained under an inert gas, with or without heating. As used herein, the term "inert gas" refers to a gas which does not undergo chemical reactions under a set of given conditions, such as those disclosed for preparing a reaction herein.

All of the components of the reactions disclosed herein can be mixed together at the same time and brought to the desired reaction temperature, whereupon the temperature is maintained with or without stirring until the desired poly alpha-1,3-1,6-glucan ether compound is formed. Alternatively, the mixed components can be left at ambient temperature as described above.

Following etherification, the pH of a reaction can be neutralized. Neutralization of a reaction can be performed using one or more acids. The term "neutral pH" as used herein, refers to a pH that is neither substantially acidic or basic (e.g., a pH of about 6-8, or about 6.0, 6.2, 6.4, 6.6, 6.8, 7.0, 7.2, 7.4, 7.6, 7.8, or 8.0). Various acids that can be used for this purpose include, but are not limited to, sulfuric, acetic (e.g., glacial acetic), hydrochloric, nitric, any mineral (inorganic) acid, any organic acid, or any combination of these acids.

A poly alpha-1,3-1,6-glucan ether compound produced in a reaction herein can optionally be washed one or more times with a liquid that does not readily dissolve the compound. For example, poly alpha-1,3-1,6-glucan ether can typically be washed with alcohol, acetone, aromatics, or any combination of these, depending on the solubility of the ether compound therein (where lack of solubility is desirable for washing). In general, a solvent comprising an organic solvent such as alcohol is preferred for washing a poly alpha-1,3-1,6-glucan ether. A poly alpha-1,3-1,6-glucan ether product can be washed one or more times with an aqueous solution containing methanol or ethanol, for example. For example, 70-95 wt % ethanol can be used to wash the product. A poly alpha-1,3-1,6-glucan ether product can be washed with a methanol:acetone (e.g., 60:40) solution in another embodiment.

A poly alpha-1,3-1,6-glucan ether produced in the disclosed reaction can be isolated. This step can be performed before or after neutralization and/or washing steps using a funnel, centrifuge, press filter, or any other method or equipment known in the art that allows removal of liquids from solids. An isolated poly alpha-1,3-1,6-glucan ether product can be dried using any method known in the art, such as vacuum drying, air drying, or freeze drying.

Any of the above etherification reactions can be repeated using a poly alpha-1,3-1,6-glucan ether product as the starting material for further modification. This approach may be suitable for increasing the DoS of an organic group, and/or adding one or more different organic groups to the ether product.

The structure, molecular weight and DoS of a poly alpha-1,3-1,6-glucan ether product can be confirmed using various physiochemical analyses known in the art such as NMR spectroscopy and size exclusion chromatography (SEC).

Any of the embodiments of poly alpha-1,3-1,6-glucan described above can be used in an etherification reaction herein. For example, the poly alpha-1,3-1,6-glucan used in an etherification reaction herein can be a product of a glucosyltransferase enzyme comprising an amino acid sequence that is at least 90% identical to SEQ ID NO:2, SEQ ID NO:4, SEQ ID NO:6, SEQ ID NO:8, or SEQ ID NO:10. Alternatively, the glucosyltransferase enzyme can comprise an amino acid sequence that is at least 91%, 92%, 93%, 94%, 95%, 96%, 97%, 98%, or 99% identical to, or 100% identical to, SEQ ID NO:2, SEQ ID NO:4, SEQ ID NO:6, SEQ ID NO:8, or SEQ ID NO:10.

Poly alpha-1,3-1,6-glucan used for preparing poly alpha-1,3-1,6-glucan ether compounds herein can be enzymatically produced from sucrose using one or more glucosyltransferase (gtf) enzymes. The poly alpha-1,3-1,6-glucan product of this enzymatic reaction can be purified before using it to prepare an ether. Alternatively, a poly alpha-1,3-1,6-glucan product of a gtf reaction can be used with little or no processing for preparing poly alpha-1,3-1,6-glucan ether compounds.

A poly alpha-1,3-1,6-glucan slurry can be used directly in any of the above processes for producing a poly alpha-1,3-1,6-glucan ether compound disclosed herein. As used herein, a "poly alpha-1,3-1,6-glucan slurry" refers to a mixture comprising the components of a gtf enzymatic reaction. A gtf enzymatic reaction can include, in addition to poly alpha-1,3-1,6-glucan itself, various components such as sucrose, one or more gtf enzymes, glucose, fructose, leucrose, buffer, FermaSure®, soluble oligosaccharides, oligosaccharide primers, bacterial enzyme extract components, borates, sodium hydroxide, hydrochloric acid, cell lysate, proteins and/or nucleic acids. Minimally, the components of a gtf enzymatic reaction can include, in addition to poly alpha-1,3-1,6-glucan itself, sucrose, one or more gtf enzymes, glucose and fructose, for example. In another example, the components of a gtf enzymatic reaction can include, in addition to poly alpha-1,3-1,6-glucan itself, sucrose, one or more gtf enzymes, glucose, fructose, leucrose and soluble oligosaccharides (and optionally bacterial enzyme extract components). It should be apparent that poly alpha-1,3-1,6-glucan, when in a slurry as disclosed herein, has not been purified or washed. It should also be apparent that a slurry represents a gtf enzymatic reaction that is complete or for which an observable amount of poly alpha-1,3-1,6-glucan has been produced, which forms a solid since it is insoluble in the aqueous reaction milieu (pH of 5-7, for example). A poly alpha-1,3-1,6-glucan slurry can be prepared by setting up a gtf reaction as disclosed herein.

Alternatively, a wet cake of poly alpha-1,3-1,6-glucan can be used directly in any of the above processes for producing a poly alpha-1,3-1,6-glucan ether compound disclosed herein. A "wet cake of poly alpha-1,3-1,6-glucan" as used herein refers to poly alpha-1,3-1,6-glucan that has been separated (e.g., filtered) from a slurry and washed with water or an aqueous solution. A wet cake can be washed at least 1, 2, 3, 4, 5, or more times, for example. The poly alpha-1,3-1,6-glucan is not dried when preparing a wet cake. A wet cake is termed as "wet" given the retention of water by the washed poly alpha-1,3-1,6-glucan.

A wet cake of poly alpha-1,3-1,6-glucan can be prepared using any device known in the art for separating solids from liquids, such as a filter or centrifuge. For example, poly alpha-1,3-1,6-glucan solids in a slurry can be collected on a funnel using a mesh screen over filter paper. Filtered wet cake can be resuspended in water (e.g., deionized water) and filtered one or more times to remove soluble components of the slurry such as sucrose, fructose and leucrose. As another example for preparing a wet cake, poly alpha-1,3-1,6-glucan solids from a slurry can be collected as a pellet via centrifugation, resuspended in water (e.g., deionized water), and re-pelleted and resuspended one or more additional times.

Non-limiting examples of compositions and methods disclosed herein include:

1. A reaction solution comprising water, sucrose and a glucosyltransferase enzyme that synthesizes poly alpha-1,3-1,6-glucan, wherein the glucosyltransferase enzyme comprises an amino acid sequence that is at least 90% identical to SEQ ID NO:2, SEQ ID NO:4, SEQ ID NO:6, SEQ ID NO:8, or SEQ ID NO:10.
2. The reaction solution of embodiment 1, wherein
   (i) at least 30% of the glycosidic linkages of the glucan are alpha-1,3 linkages,
   (ii) at least 30% of the glycosidic linkages of the glucan are alpha-1,6 linkages, and
   (iii) the glucan has a weight average degree of polymerization ($DP_w$) of at least 1000.
3. The reaction solution of embodiment 1 or 2, wherein at least 60% of the glycosidic linkages of the glucan are alpha-1,6 linkages.
4. The reaction solution of embodiment 1, 2, or 3, wherein the $DP_w$ of the glucan is at least 10000.
5. The reaction solution of embodiment 1, 2, 3 or 4, wherein the glucosyltransferase enzyme comprises the amino acid sequence of SEQ ID NO:2, SEQ ID NO:4, SEQ ID NO:6, SEQ ID NO:8, or SEQ ID NO:10.
6. A method for producing poly alpha-1,3-1,6-glucan comprising:
   a) contacting at least water, sucrose, and a glucosyltransferase enzyme that synthesizes poly alpha-1,3-1,6-glucan, wherein the glucosyltransferase enzyme comprises an amino acid sequence that is at least 90% identical to SEQ ID NO:2, SEQ ID NO:4, SEQ ID NO:6, SEQ ID NO:8, or SEQ ID NO:10; whereby poly alpha-1,3-1, 6-glucan is produced; and
   b) optionally, isolating the poly alpha-1,3-1,6-glucan produced in step (a).
7. The method of embodiment 6, wherein
   (i) at least 30% of the glycosidic linkages of the glucan are alpha-1,3 linkages,
   (ii) at least 30% of the glycosidic linkages of the glucan are alpha-1,6 linkages, and
   (iii) the glucan has a weight average degree of polymerization ($DP_w$) of at least 1000.
8. The method of embodiment 6 or 7, wherein at least 60% of the glycosidic linkages of the glucan are alpha-1,6 linkages.
9. The method of embodiment 6, 7, or 8, wherein the $DP_w$ of the glucan is at least 10000.

EXAMPLES

The disclosed invention is further defined in Examples 1-8 provided below. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meanings of some of the abbreviations used herein are as follows: "g" means gram(s), "h" means hour(s), "mL" means milliliter(s), "psi" means pound(s) per square inch, "wt %" means weight percentage, "μm" means micrometer(s), "° C." means degrees Celsius, "mg" means milligram(s), "mm" means millimeter(s), "A" means microliter(s), "mmol" means millimole(s), "min" means minute(s), "mol %" means mole percent, "M" means molar, "mM" means millimolar, "N" means normal, "rpm" means revolutions per minute, "w/v" means weight for volume, "MPa" means megaPascal(s), "LB means Luria broth, "nm means nanometer(s), "OD" means optical density, "IPTG" means isopropyl-beta-D-thio-galactoside, "xg" means gravitational force, "SDS-PAGE" means sodium dodecyl sulfate polyacrylamide electrophoresis, "DTT" means dithiothreitol, "BCA" means bicinchoninic acid, "DMAc" means N,N'-dimethyl acetamide, "DMSO" means dimethylsulfoxide, "NMR" means nuclear magnetic resonance, "SEC" means size exclusion chromatography, "DI water" means deionized water.

Materials

T10 dextran (D9260), IPTG, (cat#I6758), triphenyltetrazolium chloride, and BCA protein assay kit/reagents were obtained from the Sigma Co. (St. Louis, Mo.). BELLCO spin flasks were from the Bellco Co. (Vineland, N.J.). LB medium was from Becton, Dickinson and Company (Franklin Lakes, N.J.). Suppressor 7153 antifoam was obtained from Cognis Corporation (Cincinnati, Ohio). All other chemicals were obtained from commonly used suppliers of such chemicals.

Seed Medium

The seed medium used to grow starter cultures for the fermenters contained: yeast extract (AMBEREX 695, 5.0 grams per liter, g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 using either 5N NaOH or $H_2SO_4$ and the medium was sterilized in the flask. Post-sterilization additions included glucose (20 mL/L of a 50% w/w solution) and ampicillin (4 mL/L of a 25 mg/mL stock solution).

Fermenter Medium

The growth medium used in the fermenter contained: $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (AMBEREX 695, 5.0 g/L), Suppressor 7153 antifoam (0.25 mL/L), NaCl (1.0 g/L), $CaCl_2$ dihydrate (10 g/L), and NIT trace elements solution (10 mL/L). The NIT trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post-sterilization additions included glucose (12.5 g/L of a 50% w/w solution) and ampicillin (4 mL/L of a 25 mg/mL stock solution).

General Methods

Production of Recombinant Glucosyltransferase (Gtf) Enzymes in Fermentation

Production of a recombinant gtf enzyme in a fermenter was initiated by preparing a pre-seed culture of an *E. coli* strain expressing the gtf enzyme. A 10-mL aliquot of seed medium was added into a 125-mL disposable baffled flask and inoculated with a 1.0-mL aliquot of the *E. coli* strain in 20% glycerol. The culture was allowed to grow at 37° C. while shaking at 300 rpm for 3 hours.

A seed culture, which was used for starting growth for gtf fermentation, was prepared by charging a 2-L shake flask with 0.5 L of seed medium. 1.0 mL of the pre-seed culture was aseptically transferred into 0.5-L seed medium in the flask and cultivated at 37° C. and 300 rpm for 5 hours. The seed culture was transferred at an optical density 550 nm ($OD_{550}$)>2 to a 14-L fermenter (Braun, Perth Amboy, N.J.) containing 8 L of fermenter medium at 37° C.

The *E. coli* strain was allowed to grow in the fermenter medium. Glucose (50% w/w glucose solution containing 1% w/w $MgSO_4.7H_2O$) was fed to this culture when its glucose concentration decreased to 0.5 g/L. The glucose feed was started at 0.36 grams feed per minute (g feed/min) and increased progressively each hour to 0.42, 0.49, 0.57, 0.66, 0.77, 0.90, 1.04, 1.21, 1.41 1.63, 1.92, and 2.2 g feed/min, respectively. The feed rate remained constant afterwards. Glucose concentration in the medium was monitored using an YSI glucose analyzer (YSI, Yellow Springs, Ohio). When glucose concentration exceeded 0.1 g/L, the feed rate was decreased or stopped temporarily. Induction of gtf enzyme expression, which was performed when cells reached an $OD_{550}$ of 70, was initiated by adding 9 mL of 0.5 M IPTG. The dissolved oxygen (DO) concentration was controlled at 25% of air saturation. The DO was controlled first by impeller agitation rate (400 to 1200 rpm) and later by aeration rate (2 to 10 standard liters per minute, slpm). Culture pH was controlled at 6.8 using $NH_4OH$ (14.5% w/v) and $H_2SO_4$ (20% w/v). Back pressure was maintained at 0.5 bars. At various intervals (20, 25 and 30 hours), 5 mL of Suppressor 7153 antifoam was added to the fermenter to suppress foaming. Cells were harvested by centrifugation 8 hours post IPTG addition and were stored at −80° C. as a cell paste.

The cell paste obtained from fermentation for each gtf enzyme was suspended at 150 g/L in 50 mM potassium phosphate buffer, pH 7.2, to prepare a slurry. The slurry was homogenized at 12,000 psi (Rannie-type machine, APV-1000 or APV 16.56) and the homogenate chilled to 4° C. With moderately vigorous stirring, 50 g of a floc solution (Sigma Aldrich no. 409138, 5% in 50 mM sodium phosphate buffer, pH 7.0) was added per liter of cell homogenate. Agitation was reduced to light stirring for 15 minutes. The cell homogenate was then clarified by centrifugation at 4500 rpm for 3 hours at 5-10° C. Supernatant, containing gtf enzyme, was concentrated (approximately 5×) with a 30 kiloDalton (kDa) cut-off membrane to render a gtf extract.

Determination of Gtf Enzymatic Activity

Gtf enzyme activity was confirmed by measuring the production of reducing sugars (fructose and glucose) in a gtf reaction solution. A reaction solution was prepared by adding a gtf extract (prepared as above) to a mixture containing sucrose (50 g/L), potassium phosphate buffer (pH 6.5, 50 mM), and dextran T10 (1 mg/mL); the gtf extract was added to 5% by volume. The reaction solution was then incubated at 22-25° C. for 24-30 hours, after which it was centrifuged. Supernatant (0.01 mL) was added to a mixture containing 1 N NaOH and 0.1% triphenyltetrazolium chloride (Sigma- Aldrich). The mixture was incubated for five minutes after which its $OD_{480\ nm}$ was determined using an ULTROSPEC spectrophotometer (Pharmacia LKB, New York, N.Y.) to gauge the presence of the reducing sugars fructose and glucose.

Determination of Glycosidic Linkages

Glycosidic linkages in glucan products synthesized by a gtf enzyme were determined by $^{13}C$ NMR (nuclear magnetic resonance) or $^1H$ NMR.

For $^{13}C$ NMR, dry glucan polymer (25-30 mg) was dissolved in 1 mL of deuterated DMSO containing 3% by weight of LiCl with stirring at 50° C. Using a glass pipet, 0.8 mL of the solution was transferred into a 5-mm NMR tube. A quantitative $^{13}C$ NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 pulses. The time domain data was transformed using an exponential multiplication of 2.0 Hz.

For $^1H$ NMR, approximately 20 mg of a glucan polymer sample was weighed into a vial on an analytical balance. The vial was removed from the balance and 0.8 mL of deuterated DMSO (DMSO-d6), containing 3% by weight of LiCl, was added to the vial. The mixture was stirred with a magnetic stir bar and warmed to 90° C. until the glucan sample dissolved. The solution was allowed to cool to room temperature. While stirring at room temperature, 0.2 mL of a 20% by volume solution of trifluoroacetic acid (TFA) in DMSO-d6 was added to the polymer solution. The TFA was added in order to move all hydroxyl proton signals out of the region of the spectrum where carbohydrate ring proton signals occur. A portion, 0.8 mL, of the final solution was transferred, using a glass pipet, into a 5-mm NMR tube. A quantitative $^1H$ NMR spectrum was acquired using an NMR spectrometer with a proton frequency of 500 MHz or greater. The spectrum was acquired using a spectral window of 11.0 ppm and a transmitter offset of 5.5 ppm. A 90° pulse was applied for 32 pulses with an inter-pulse delay of 10 seconds and an acquisition time of 1.5 seconds. The time domain data were transformed using an exponential multiplication of 0.15 Hz.

Determination of Weight Average Degree of Polymerization ($DP_w$)

The $DP_w$ of a glucan product synthesized by a gtf enzyme was determined by SEC. Dry glucan polymer was dissolved in DMAc and 5% LiCl (0.5 mg/mL) with shaking overnight at 100° C. The SEC system used was an Alliance™ 2695 separation module from Waters Corporation (Milford, Mass.) coupled with three online detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration).

Example 1

Production of Gtf Enzyme 4297 (SEQ ID NO:2)

This Example describes preparing an N-terminally truncated version of a *Streptococcus oralis* gtf enzyme identified in GENBANK under GI number 7684297 (SEQ ID NO:2, encoded by SEQ ID NO:1; herein referred to as "4297").

A nucleotide sequence encoding gtf 4297 was synthesized using codons optimized for protein expression in *E. coli* (DNA2.0, Inc., Menlo Park, Calif.). The nucleic acid product (SEQ ID NO:1), encoding gtf 4297 (SEQ ID NO:2), was subcloned into pJexpress404® (DNA2.0, Inc.) to generate the plasmid construct identified as pMP70. This plasmid construct was used to transform *E. coli* MG1655 (ATCC™ 47076) cells to generate the strain identified as MG1655/pMP70.

Production of gtf 4297 by bacterial expression and determination of its enzymatic activity were performed following the procedures disclosed in the General Methods section. The linkage profile and $DP_w$ of glucan produced by 4297 are shown in Table 2 (see Example 6 below).

Example 2

Production of Gtf Enzyme 3298 (SEQ ID NO:4)

This Example describes preparing an N-terminally truncated version of a *Streptococcus* sp. C150 gtf enzyme identified in GENBANK under GI number 322373298 (SEQ ID NO:4, encoded by SEQ ID NO:3; herein referred to as "3298").

A nucleotide sequence encoding gtf 3298 was synthesized using codons optimized for protein expression in *E. coli* (DNA2.0, Inc.). The nucleic acid product (SEQ ID NO:3), encoding gtf 3298 (SEQ ID NO:4), was subcloned into pJexpress404® to generate the plasmid construct identified as pMP98. This plasmid construct was used to transform *E. coli* MG1655 (ATCC™ 47076) cells to generate the strain identified as MG1655/pMP98.

Production of gtf 3298 by bacterial expression and determination of its enzymatic activity were performed following the procedures disclosed in the General Methods section. The linkage profile and $DP_w$ of glucan produced by 3298 are shown in Table 2 (see Example 6 below).

Example 3

Production of Gtf Enzyme 0544 (SEQ ID NO:6) This Example describes preparing an N-terminally truncated version of a *Streptococcus mutans* gtf enzyme identified in GENBANK under GI number 290580544 (SEQ ID NO:6, encoded by SEQ ID NO:5; herein referred to as "0544").

A nucleotide sequence encoding gtf 0544 was synthesized using codons optimized for protein expression in *E. coli* (DNA2.0, Inc.). The nucleic acid product (SEQ ID NO:5), encoding gtf 0544 (SEQ ID NO:6), was subcloned into pJexpress404® to generate the plasmid construct identified as pMP67. This plasmid construct was used to transform *E. coli* MG1655 (ATCC™ 47076) cells to generate the strain identified as MG1655/pMP67.

Production of gtf 0544 by bacterial expression and determination of its enzymatic activity were performed following the procedures disclosed in the General Methods section.

The linkage profile and $DP_w$ of glucan produced by 0544 are shown in Table 2 (see Example 6 below).

Example 4

Production of Gtf Enzyme 5618 (SEQ ID NO:8)

This Example describes preparing an N-terminally truncated version of a *Streptococcus sanguinis* gtf enzyme identified in GENBANK under GI number 328945618 (SEQ ID NO:8, encoded by SEQ ID NO:7; herein referred to as "5618").

A nucleotide sequence encoding gtf 5618 was synthesized using codons optimized for protein expression in *E. coli* (DNA2.0, Inc.). The nucleic acid product (SEQ ID NO:7), encoding gtf 5618 (SEQ ID NO:8), was subcloned into pJexpress404® to generate the plasmid construct identified as pMP72. This plasmid construct was used to transform *E. coli* MG1655 (ATCC™ 47076) cells to generate the strain identified as MG1655/pMP72.

Production of gtf 5618 by bacterial expression and determination of its enzymatic activity were performed following the procedures disclosed in the General Methods section. The linkage profile and $DP_w$ of glucan produced by 5618 are shown in Table 2 (see Example 6 below).

Example 5

Production of Gtf Enzyme 2379 (SEQ ID NO:10)

This Example describes preparing an N-terminally truncated version of a *Streptococcus salivarius* gtf enzyme identified in GENBANK under GI number 662379 (SEQ ID NO:10, encoded by SEQ ID NO:9; herein referred to as "2379").

A nucleotide sequence encoding gtf 2379 was synthesized using codons optimized for protein expression in *E. coli* (DNA2.0, Inc.). The nucleic acid product (SEQ ID NO:9), encoding gtf 2379 (SEQ ID NO:10), was subcloned into pJexpress404® to generate the plasmid construct identified as pMP65. This plasmid construct was used to transform *E. coli* MG1655 (ATCC™ 47076) cells to generate the strain identified as MG1655/pMP65.

Production of gtf 2379 by bacterial expression and determination of its enzymatic activity were performed following the procedures disclosed in the General Methods section. The linkage profile and $DP_w$ of glucan produced by 2379 are shown in Table 2 (see Example 6 below).

Example 6

Production of Insoluble Glucan Polymer with Gtf Enzymes

This Example describes using the gtf enzymes prepared in the above Examples to synthesize glucan polymer.

Reactions were performed with each of the above gtf enzymes following the procedures disclosed in the General Methods section. Briefly, gtf reaction solutions were prepared comprising sucrose (50 g/L), potassium phosphate buffer (pH 6.5, 50 mM) and a gtf enzyme (2.5% extract by volume). After 24-30 hours at 22-25° C., insoluble glucan polymer product was harvested by centrifugation, washed three times with water, washed once with ethanol, and dried at 50° C. for 24-30 hours.

Following the procedures disclosed in the General Methods section, the glycosidic linkages in the insoluble glucan polymer product from each reaction were determined by $^{13}C$ NMR, and the $DP_w$ for each product was determined by SEC. The results of these analyses are shown in Table 2.

TABLE 2

Linkages and $DP_w$ of Glucan Produced by Various Gtf Enzymes

| Gtf | SEQ ID NO. | Glucan Alpha Linkages | | $DP_w$ |
|---|---|---|---|---|
| | | % 1,3 | % 1,6 | |
| 4297 | 2 | 31 | 67 | 10540 |
| 3298 | 4 | 50 | 50 | 1235 |
| 0544 | 6 | 62 | 36 | 3815 |
| 5618 | 8 | 34 | 66 | 3810 |
| 2379 | 10 | 37 | 63 | 1640 |

Thus, gtf enzymes capable of producing insoluble glucan polymer having a heterogeneous glycosidic linkage profile (alpha-1,3 and 1,6 linkages) and a $DP_w$ of at least 1000 were identified. These enzymes can be used to produce insoluble poly alpha-1,3-1,6-glucan suitable for derivatization to downstream products such as glucan ether, as demonstrated below in Example 7.

Example 7

Preparation of Carboxymethyl Poly Alpha-1,3-1,6-Glucan

This Example describes producing the glucan ether derivative, carboxymethyl poly alpha-1,3-1,6-glucan.

Poly alpha-1,3-1,6-glucan was first prepared as in Example 6, but with a few modifications. Specifically, a glucan polymerization reaction solution was prepared comprising sucrose (300 g), potassium phosphate buffer (pH 5.5; 8.17 g), gtf enzyme 4297 extract (90 mL) in 3 L distilled water. After 24-30 hours at 22-25° C., insoluble glucan polymer was harvested by centrifugation, filtered, washed three times with water, washed twice with ethanol, and dried at 50° C. for 24-30 hours. About 12 g of poly alpha-1,3-1, 6-glucan was obtained.

The $DP_w$ and glycosidic linkages of the insoluble glucan polymer was determined as described in the General Methods. The polymer had a DPw of 10,540 and a linkage profile of 31% alpha-1,3 and 67% alpha-1,6. It had a weight-average molecular weight ($M_w$) of 1100000. This solid glucan was used to prepare carboxymethyl poly alpha-1,3-1,6-glucan as follows.

1 g of the poly alpha-1,3-1,6-glucan was added to 20 mL of isopropanol in a 50-mL capacity round bottom flask fitted with a thermocouple for temperature monitoring and a condenser connected to a recirculating bath, and a magnetic stir bar. Sodium hydroxide (40 mL of a 15% solution) was added dropwise to the preparation, which was then heated to 25° C. on a hotplate. The preparation was stirred for 1 hour before the temperature was increased to 55° C. Sodium monochloroacetate (0.3 g) was then added to provide a reaction, which was held at 55° C. for 3 hours before being neutralized with glacial acetic acid. The solid material was then collected by vacuum filtration and washed with ethanol (70%) four times, dried under vacuum at 20-25° C., and analyzed by NMR to determine degree of substitution (DoS) of the solid. The solid was identified as sodium carboxymethyl poly alpha-1,3-1,6-glucan with a DoS of 0.464 (sample 1D in Table 3).

Table 3 provides a list of DoS measurements for additional samples of carboxymethyl poly alpha-1,3-1,6-glucan prepared using processes similar to the above process, but with certain modifications as indicated in the table. Each reaction listed in Table 3 used poly alpha-1,3-1,6-glucan with an $M_w$ of 1100000 as substrate. The results in Table 3 indicate that by altering the reagent amounts and time of the etherification reaction, product DoS can be altered.

TABLE 3

Samples of Sodium Carboxymethyl Poly Alpha-1,3-1,6-Glucan Prepared from Poly Alpha-1,3-1,6-Glucan

| Product Sample Designation | Reagent[a]:Glucan Molar Ratio[b] | NaOH:Glucan Molar Ratio[b] | Reaction Time (hours) | DoS |
|---|---|---|---|---|
| 1A | 1.66 | 1.68 | 3 | 0.827 |
| 1B | 0.83 | 1.92 | 1.5 | 0.648 |
| 1C | 0.83 | 1.08 | 3 | 0.627 |
| 1D | 0.41 | 1.08 | 3 | 0.464 |

[a]Reagent refers to sodium monochloroacetate.
[b]Molar ratios calculated as moles of reagent per moles of poly alpha-1,3-1,6-glucan (second column), or moles of NaOH per moles of poly alpha-1,3-1,6-glucan (third column).

Thus, the glucan ether derivative, carboxymethyl poly alpha-1,3-1,6-glucan, was prepared and isolated.

Example 8

Viscosity Modification Using Carboxymethyl Poly Alpha-1,3-1,6-Glucan

This Example describes the effect of carboxymethyl poly alpha-1,3-1,6-glucan on the viscosity of an aqueous composition.

Various sodium carboxymethyl poly alpha-1,3-1,6 glucan samples (1A-1D) were prepared as described in Example 72. To prepare 0.6 wt % solutions of each of these samples, 0.102 g of sodium carboxymethyl poly alpha-1,3-1,6-glucan was added to DI water (17 g). Each preparation was then mixed using a bench top vortexer at 1000 rpm until the solid was completely dissolved.

To determine the viscosity of carboxymethyl poly alpha-1,3-1,6-glucan, each solution of the dissolved glucan ether samples was subjected to various shear rates using a Brookfield III+ viscometer equipped with a recirculating bath to control temperature (20° C.). The shear rate was increased using a gradient program which increased from 0.1-232.5 rpm and the shear rate was increased by 4.55 (1/s) every 20 seconds. Results of this experiment at 14.72 (1/s) are listed in Table 4.

TABLE 4

Viscosity of Carboxymethyl Poly Alpha-1,3-1,6-Glucan Solutions at Various Shear Rates

| Sample | Sample Loading (wt %) | Viscosity (cPs) |
|---|---|---|
| 1A | 0.6 | 106.35[a] |
| 1B | 0.6 | 48.92[a] |
| 1C | 0.6 | 633.83[a] |
| 1D | 0.6 | 2008.45[b] |

[a]Viscosity at 14.72 rpm.
[b]Viscosity at 17.04 rpm

The results summarized in Table 4 indicate that a low concentration (0.6 wt %) of carboxymethyl poly alpha-1,3-1,6-glucan can increase the viscosity of DI water when dissolved therein. Also, the results in Table 4 indicate that a relatively low DoS (e.g., as low as 0.464, refer to sample 1D in Tables 3 and 4) is sufficient for carboxymethyl poly alpha-1,3-1,6-glucan to be an effective viscosity modifier of an aqueous composition.

It is noteworthy that the viscosity levels obtained with carboxymethyl poly alpha-1,3-1,6-glucan are substantially higher than the viscosity levels observed using carboxymethyl dextran (refer to comparative Example 10) and carboxymethyl poly alpha-1,3-glucan (refer to comparative Example 12) (compare Table 4 with Tables 6 and 8). This was despite these other agents having DoS levels similar with those of the above carboxymethyl poly alpha-1,3-1,6-glucan samples (compare Table 3 with Tables 5 and 7) and using these other agents at the same concentration (0.6 wt %).

Example 9 (Comparative)

Preparation of Carboxymethyl Dextran from Solid Dextran

This Example describes producing carboxymethyl dextran for use in Example 10.

0.5 g of solid dextran ($M_w$=750000) was added to 10 mL of isopropanol in a 50-mL capacity round bottom flask fitted with a thermocouple for temperature monitoring and a condenser connected to a recirculating bath, and a magnetic stir bar. Sodium hydroxide (0.9 mL of a 15% solution) was added dropwise to the preparation, which was then heated to 25° C. on a hotplate. The preparation was stirred for 1 hour before the temperature was increased to 55° C. Sodium monochloroacetate (0.15 g) was then added to provide a reaction, which was held at 55° C. for 3 hours before being neutralized with glacial acetic acid. The solid material was then collected by vacuum filtration and washed with ethanol (70%) four times, dried under vacuum at 20-25° C., and analyzed by NMR to determine degree of substitution (DoS) of the solid. The solid was identified as sodium carboxymethyl dextran.

Additional sodium carboxymethyl dextran was prepared using dextran of different $M_w$. The DoS values of carboxymethyl dextran samples prepared in this example are provided in Table 5.

TABLE 5

Samples of Sodium Carboxymethyl Dextran Prepared from Solid Dextran

| Product Sample Designation | Dextran $M_w$ | Reagent[a]:Dextran Molar Ratio[b] | NaOH:Dextran Molar Ratio[b] | Reaction Time (hours) | DoS |
|---|---|---|---|---|---|
| 2A | 750000 | 0.41 | 1.08 | 3 | 0.64 |
| 2B | 1750000 | 0.41 | 0.41 | 3 | 0.49 |

[a]Reagent refers to sodium monochloroacetate.
[b]Molar ratios calculated as moles of reagent per moles of dextran (third column), or moles of NaOH per moles of dextran (fourth column).

These carboxymethyl dextran samples were tested for their viscosity modification effects in Example 10.

Example 10 (Comparative)

Effect of Shear Rate on Viscosity of Carboxymethyl Dextran

This Example describes the viscosity, and the effect of shear rate on viscosity, of solutions containing the carboxymethyl dextran samples prepared in Example 9.

Various sodium carboxymethyl dextran samples (2A and 2B) were prepared as described in Example 9. To prepare 0.6 wt % solutions of each of these samples, 0.102 g of sodium carboxymethyl dextran was added to DI water (17 g). Each preparation was then mixed using a bench top vortexer at 1000 rpm until the solid was completely dissolved.

To determine the viscosity of carboxymethyl dextran at various shear rates, each solution of the dissolved dextran ether samples was subjected to various shear rates using a Brookfield III+ viscometer equipped with a recirculating bath to control temperature (20° C.). The shear rate was increased using a gradient program which increased from 0.1-232.5 rpm and the shear rate was increased by 4.55 (1/s) every 20 seconds. The results of this experiment at 14.72 (1/s) are listed in Table 6.

TABLE 6

Viscosity of Carboxymethyl Dextran Solutions at Various Shear Rates

| Sample | Sample Loading (wt %) | Viscosity (cPs) @ 66.18 rpm | Viscosity (cPs) @ 110.3 rpm | Viscosity (cPs) @ 183.8 rpm | Viscosity (cPs) @ 250 rpm |
|---|---|---|---|---|---|
| 2A | 0.6 | 4.97 | 2.55 | 4.43 | 3.88 |
| 2B | 0.6 | 6.86 | 5.68 | 5.28 | 5.26 |

The results summarized in Table 6 indicate that 0.6 wt % solutions of carboxymethyl dextran have viscosities of about 2.5-7 cPs. These viscosity levels are substantially lower than the viscosity levels observed using carboxymethyl poly alpha-1,3-1,6-glucan samples at the same low concentration (0.6 wt %) in water. Specifically, Table 4 indicates that carboxymethyl poly alpha-1,3-1,6-glucan solutions have viscosities of about 48-2010 cPs. This difference in viscosity modification is further noteworthy with respect to carboxymethyl dextran sample 2B, which likely has a higher molecular weight than the molecular weights of the carboxymethyl poly alpha-1,3-1,6-glucan samples. Despite having a higher molecular weight, carboxymethyl dextran sample 2B exhibited a substantially lower viscosity-modifying effect than carboxymethyl poly alpha-1,3-1,6-glucan.

Thus, it is believed that carboxymethyl poly alpha-1,3-1,6-glucan has a greater viscosity-modifying effect than carboxymethyl dextran.

Example 11 (Comparative)

Preparation of Carboxymethyl Poly Alpha-1,3-Glucan

This Example describes producing carboxymethyl poly alpha-1,3-glucan for use in Example 12.

Poly alpha-1,3-glucan was prepared using a gtfJ enzyme preparation as described in U.S. Patent Appl. Publ. No. 2013/0244288, which is incorporated herein by reference in its entirety.

150 g of poly alpha-1,3-glucan ($M_w$=192000) was added to 3000 mL of isopropanol in a 500-mL capacity round bottom flask fitted with a thermocouple for temperature monitoring and a condenser connected to a recirculating bath, and a magnetic stir bar. Sodium hydroxide (600 mL of a 15% solution) was added dropwise to the preparation, which was then heated to 25° C. on a hotplate. The preparation was stirred for 1 hour before the temperature was increased to 55° C. Sodium monochloroacetate was then added to provide a reaction, which was held at 55° C. for 3 hours before being neutralized with 90% acetic acid. The solid material was then collected by vacuum filtration and washed with ethanol (70%) four times, dried under vacuum at 20-25° C., and analyzed by NMR to determine degree of substitution (DoS) of the solid. The solid was identified as sodium carboxymethyl poly alpha-1,3-glucan.

Additional sodium carboxymethyl poly alpha-1,3-glucan was prepared using processes similar to the above process, but with certain modifications as indicated in the Table 7. Each reaction listed in Table 7 used poly alpha-1,3-glucan with an $M_w$ of 192000 as substrate.

TABLE 7

Samples of Carboxymethyl Poly Alpha-1,3-Glucan

| Product Sample Designation | Reagent[a]:Glucan Molar Ratio[b] | NaOH:Glucan Molar Ratio[b] | Reaction Time (hours) | DoS |
|---|---|---|---|---|
| C1A | 3.297 | 2.4 | 3 | 0.977 |
| C1B | 1.65 | 2.4 | 3 | 0.514 |

[a]Reagent refers to sodium monochloroacetate.
[b]Molar ratios calculated as moles of reagent per moles of poly alpha-1,3-glucan (second column), or moles of NaOH per moles of poly alpha-1,3- glucan (third column).

These carboxymethyl poly alpha-1,3-glucan samples were tested for their viscosity modification effects in Example 12.

Example 12 (Comparative)

Viscosity Modification Using Carboxymethyl Poly Alpha-1,3-Glucan

This Example describes the effect of carboxymethyl poly alpha-1,3-glucan on the viscosity of an aqueous composition.

Various sodium carboxymethyl poly alpha-1,3-glucan samples (C1A and C1B) were prepared as described in Example 11. To prepare 0.6 wt % solutions of each of these samples, 0.102 g of sodium carboxymethyl poly alpha-1,3-glucan was added to DI water (17 g). Each preparation was then mixed using a bench top vortexer at 1000 rpm until the solid was completely dissolved.

To determine the viscosity of carboxymethyl poly alpha-1,3-glucan at various shear rates, each solution of the dissolved glucan ether samples was subjected to various shear rates using a Brookfield III+ viscometer equipped with a recirculating bath to control temperature (20° C.). The shear rate was increased using a gradient program which increased from 0.1-232.5 rpm and the shear rate was increased by 4.55 (1/s) every 20 seconds. Results of this experiment at 14.72 (1/s) are listed in Table 8.

TABLE 8

Viscosity of Carboxymethyl Poly Alpha-1,3-Glucan Solutions

| Sample | Sample Loading (wt %) | Viscosity (cPs) @ 14.9 rpm |
|---|---|---|
| C1A | 0.6 | 6.38 |
| C1B | 0.6 | 21.27 |

The results summarized in Table 8 indicate that 0.6 wt % solutions of carboxymethyl poly alpha-1,3-glucan have viscosities of about 6-22 cPs. These viscosity levels are lower than the viscosity levels observed using carboxymethyl poly alpha-1,3-1,6-glucan samples at the same low concentration (0.6 wt %) in water. Specifically, Table 4 indicates that carboxymethyl poly alpha-1,3-1,6-glucan solutions have viscosities of about 48-2010 cPs.

Thus, it is believed that carboxymethyl poly alpha-1,3-1,6-glucan may have a greater viscosity-modifying effect than carboxymethyl poly alpha-1,3-glucan.

Example 13 (Comparative)

Viscosity Modification Using Carboxymethyl Cellulose

This Example describes the effect of carboxymethyl cellulose (CMC) on the viscosity of an aqueous composition.

CMC samples (C3A and C3B, Table 9) obtained from DuPont Nutrition & Health (Danisco) were dissolved in DI water to prepare 0.6 wt % solutions of each sample.

To determine the viscosity of CMC at various shear rates, each solution of the dissolved CMC samples was subjected to various shear rates using a Brookfield III+ viscometer equipped with a recirculating bath to control temperature (20° C.). The shear rate was increased using a gradient program which increased from 0.1-232.5 rpm and the shear rate was increased by 4.55 (1/s) every 20 seconds. Results of this experiment at 14.72 (1/s) are listed in Table 9.

TABLE 9

Viscosity of CMC Solutions

| Sample | Molecular Weight (Mw) | DoS | Sample Loading (wt %) | Viscosity (cPs) @ 14.9 rpm |
|---|---|---|---|---|
| C3A (BAK 130) | ~130000 | 0.66 | 0.6 | 235.03 |
| C3B (BAK 550) | ~550000 | 0.734 | 0.6 | 804.31 |

CMC (0.6 wt %) therefore can increase the viscosity of an aqueous solution. However, it is believed that this ability to increase viscosity is lower than the ability of carboxymethyl poly alpha-1,3-1,6-glucan to increase viscosity.

Thus, it is believed that carboxymethyl poly alpha-1,3-1,6-glucan may have a greater viscosity-modifying effect than CMC.

What is claimed is:

1. An enzymatic reaction composition comprising water, sucrose and an isolated glucosyltransferase enzyme that synthesizes water-insoluble poly alpha-1,3-1,6-glucan, wherein said glucosyltransferase enzyme comprises an amino acid sequence that is at least 90% identical to SEQ ID NO:2.

2. The enzymatic reaction composition of claim 1, wherein said glucosyltransferase enzyme comprises an amino acid sequence that is at least 95% identical to SEQ ID NO:2.

3. The enzymatic reaction composition of claim 2, wherein said glucosyltransferase enzyme comprises an amino acid sequence that is at least 98% identical to SEQ ID NO:2.

4. The enzymatic reaction composition of claim 3, wherein said glucosyltransferase enzyme comprises an amino acid sequence that is at least 99% identical to SEQ ID NO:2.

5. The enzymatic reaction composition of claim 4, wherein said glucosyltransferase enzyme comprises the amino acid sequence of SEQ ID NO:2.

6. The enzymatic reaction composition of claim 1, wherein said glucosyltransferase enzyme consists of an amino acid sequence that is at least 90% identical to SEQ ID NO:2.

7. The enzymatic reaction composition of claim 6, wherein said glucosyltransferase enzyme consists of an amino acid sequence that is at least 95% identical to SEQ ID NO:2.

8. The enzymatic reaction composition of claim 7, wherein said glucosyltransferase enzyme consists of an amino acid sequence that is at least 98% identical to SEQ ID NO:2.

9. The enzymatic reaction composition of claim 8, wherein said glucosyltransferase enzyme consists of an amino acid sequence that is at least 99% identical to SEQ ID NO:2.

10. The enzymatic reaction composition of claim 9, wherein said glucosyltransferase enzyme consists of the amino acid sequence of SEQ ID NO:2.

11. The enzymatic reaction composition of claim 1, wherein the enzymatic reaction composition comprises only one of said glucosyltransferase enzyme.

12. The enzymatic reaction composition of claim 1, wherein the enzymatic reaction composition is cell-free.

13. A method for producing water-insoluble poly alpha-1,3-1,6-glucan, the method comprising:
    a) contacting at least water, sucrose, and an isolated glucosyltransferase enzyme in an enzymatic reaction composition, wherein said glucosyltransferase enzyme synthesizes water-insoluble poly alpha-1,3-1,6-glucan and comprises an amino acid sequence that is at least 90% identical to SEQ ID NO:2, whereby water-insoluble poly alpha-1,3-1,6-glucan is produced; and
    b) optionally, isolating the water-insoluble poly alpha-1,3-1,6-glucan produced in step (a).

14. The method of claim 13, wherein said glucosyltransferase enzyme comprises an amino acid sequence that is at least 95% identical to SEQ ID NO:2.

15. The method of claim 14, wherein said glucosyltransferase enzyme comprises an amino acid sequence that is at least 98% identical to SEQ ID NO:2.

16. The method of claim 15, wherein said glucosyltransferase enzyme comprises an amino acid sequence that is at least 99% identical to SEQ ID NO:2.

17. The method of claim 16, wherein said glucosyltransferase enzyme comprises the amino acid sequence of SEQ ID NO:2.

* * * * *

SEQUENCE LISTING

<160> NUMBER OF SEQ ID NOS: 10

<210> SEQ ID NO 1
<211> LENGTH: 4047
<212> TYPE: DNA
<213> ORGANISM: Streptococcus oralis

<400> SEQUENCE: 1

```
atgatcgacg gcaaaaacta ctacgtacag gatgatggca cggtaaagaa gaatttcgcg        60
gtagaactga atggtcgtat cctgtatttt gatgcagaaa ccggcgctct ggttgatagc       120
aacgagtatc agttccaaca gggtacgagc agcctgaaca atgaattttc tcagaagaac       180
gcattctatg gtacgaccga taaggatatt gagactgtgg atggctacct gaccgcagat       240
agctggtatc gcccgaaatt catcctgaag gatggcaaga cgtggaccgc gagcacggaa       300
acggatctgc gtccgctgtt gatggcatgg tggccggaca agcgtaccca aatcaactat       360
ctgaactaca tgaaccagca gggtctgggt gcgggtgcgt ttgagaacaa agtggagcag       420
gccctgctga cgggtgcaag ccaacaggta caacgcaaga tcgaagagaa gattggtaaa       480
gagggtgata ccaagtggct gcgcaccctg atgggtgcgt tcgtgaaaac gcaaccaaac       540
tggaatatca aaaccgagtc tgaaacgacc ggcacgaaaa aggaccatct gcaaggcggt       600
gcactgctgt atacgaacaa cgagaaatcc ccgcacgcgg acagcaaatt tcgtctgctg       660
aatcgtaccc cgaccagcca aaccggcacg ccgaagtatt tcatcgacaa gtctaacggt       720
ggctacgaat ttctgctggc gaacgatttt gacaatagca tcctgcggt acaagctgag       780 cagctgaatt ggctgcacta catgatgaac tttggcagca ttgttgcgaa tgatccgacc       840
gcgaatttcg acggcgttcg tgtggatgct gttgataacg tcaatgcgga cttgttgcaa       900
attgcaagcg attactttaa gagccgttac aaagtcggtg agagcgaaga agaagcgatc       960
aagcacctgt ccatcctgga agcatggagc gataacgacc cggactacaa caaagatacc      1020
aagggtgcac agttggcgat tgataacaaa ctgcgcctga gcctgctgta ctctttcatg      1080
cgtaatctga gcatccgtag cggtgttgaa ccgacgatta ccaatagcct gaatgaccgt      1140
tccagcgaaa agaagaacgg cgagcgtatg gcaaattaca tcttcgtgcg tgcccacgat      1200
agcgaggtcc aaacggtgat cgccgacatc attcgcgaaa acatcaatcc gaacaccgac      1260
```

```
ggcctgacgt ttacgatgga cgagctgaag caggcattca agatttacaa cgaggacatg   1320
cgcaaggcgg acaaaaagta tacccagttt aacattccta ccgcacacgc gctgatgctg   1380
tctaataagg attctattac ccgcgtgtac tatggtgatc tgtatactga cgatggtcag   1440
tacatggaga agaaaagccc gtatcacgat gcgattgacg ctctgctgcg tgcacgtatt   1500
aaatacgtcg cgggtggcca ggatatgaaa gtgacctata tgggcgtgcc gcgtgaagcg   1560
gataagtgga gctataacgg cattctgacc agcgtgcgct atggcacggg cgctaacgaa   1620
gccacggatg agggcactgc ggaaacgcgc acgcaaggta tggcagtgat tgcgagcaat   1680
aatccaaatc tgaaactgaa tgaatgggac aagttgcaag tcaacatggg tgcggcgcat   1740
aagaatcaat attaccgtcc ggttctgctg accactaagg acggtatcag ccgttatctg   1800
accgatgaag aagtgcctca gagcctgtgg aaaaagacgg acgcaaacgg tattctgacc   1860
ttcgacatga atgatattgc tggctacagc aacgtgcaag ttagcggtta cctggccgtc   1920
tgggtcccgg tcggtgcgaa ggcggatcaa gatgcgcgca cgaccgcatc caagaagaaa   1980
aatgcgtcgg gtcaggtgta cgaaagcagc gcggctctgg atagccagct gatttacgaa   2040
ggtttcagca actttcaaga ctttgccact cgcgatgatc agtacacgaa caaggtcatt   2100
gcgaaaaacg tgaatctgtt caaagaatgg ggtgtgacca gcttcgagct gccgccgcag   2160
tacgtgagca gccaagatgg caccttcctg gacagcatta tccaaaacgg ctatgcattt   2220
gaagaccgtt acgatatggc gatgagcaag aataacaagt atggtagcct gaaagacctg   2280
ttgaacgcgc tgcgcgcact gcacagcgtc aacattcaag caatcgccga ttgggtgccg   2340
gaccaaattt acaacttgcc gggcaaagag gtggtgaccg caactcgtgt caacaactac   2400
ggcacctacc gtgagggtgc tgaaatcaaa gaaaagctgt atgtcgccaa tagcaagacc   2460
aacgaaaccg atttccaagg taaatacggt ggtgcgttcc tggatgagct gaaggcgaag   2520
tacccggaga ttttcgagcg tgtccaaatc agcaacggcc aaaagatgac taccgatgaa   2580
aagatcacca aatggagcgc gaaatacttt aatggcacca atattctggg tcgtggcgcg   2640
tactatgtcc tgaaagattg ggccagcaat gattacctga cgaaccgtaa cggcgagatt   2700
gttttgccga agcaactggt taacaagaat agctataccg ctttgtcag cgacgcgaac   2760 ggcacgaagt tctattctac ctctggctac caggcgaaga acagcttcat tcaagacgaa   2820
aacggtaatt ggtattactt tgacaaacgt ggttatctgg ttacgggcgc acacgagatt   2880
gatggcaagc atgtctactt cctgaaaaac ggtatccaac tgcgtgacag catccgtgag   2940
gatgagaacg taatcaata ctattacgac cagaccggcg cacaagtgct gaaccgttac   3000
tacacgacgg acggtcagaa ttggcgctat ttcgatgcga aggtgttat ggcacgcggc   3060 ctggtaaaga ttggtgacgg ccaacagttt ttcgatgaaa acggttacca ggtcaagggc   3120
aagattgtta gcgcaaaaga cggcaagctg cgctactttg ataaagactc tggcaatgct   3180
gtcattaatc gttcgcgca gggtgacaat ccgagcgact ggtactattt cggtgtggaa   3240
tttgctaaac tgacgggttt gcaaaagatc ggccagcaga cgctgtattt tgaccaagac   3300
ggtaagcaag tcaaaggtaa gatcgtaact ctgtcggaca aaagcattcg ttacttcgat   3360
gccaacagcg gtgaaatggc ggttggcaag ttcgcggaag gtgcaaagaa tgagtggtat   3420
tatttcgata aaaccggcaa agcggttact ggtttgcaga aaattggtaa gcagaccctg   3480
tactttgacc aggacggtaa acaggttaaa ggcaaggttg tcacgctggc tgataaaagc   3540
atccgctact tcgacgcaga ctccggcgag atggcggtcg gtaagtttgc agagggtgcg   3600
```

-continued

```
aagaacgagt ggtactattt tgatcagact ggcaaggccg tgactggttt gcaaaagatt    3660
gacaagcaaa ccttgtactt cgaccaggac ggtaaacaag tcaagggtaa gattgtgacg    3720
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgtttct cgttatttcg acgcaaactc cggtgacatg    3960
gctcgttcta aatggattca actggaagat ggcagctgga tgtatttcga ccgtgacggt    4020
cgtggccaga attttggccg taactaa                                       4047
```

<210> SEQ ID NO 2
<211> LENGTH: 1348
<212> TYPE: PRT
<213> ORGANISM: Streptococcus oralis

<400> SEQUENCE: 2

```
Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
```

```
            290                 295                 300
Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Pro Asp Tyr
                325                 330                 335

Asn Lys Asp Thr Lys Gly Ala Gln Leu Ala Ile Asp Asn Lys Leu Arg
                340                 345                 350

Leu Ser Leu Leu Tyr Ser Phe Met Arg Asn Leu Ser Ile Arg Ser Gly
                355                 360                 365

Val Glu Pro Thr Ile Thr Asn Ser Leu Asn Asp Arg Ser Ser Glu Lys
                370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
                435                 440                 445

Gln Phe Asn Ile Pro Thr Ala His Ala Leu Met Leu Ser Asn Lys Asp
                450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
                500                 505                 510

Tyr Met Gly Val Pro Arg Glu Ala Asp Lys Trp Ser Tyr Asn Gly Ile
                515                 520                 525

Leu Thr Ser Val Arg Tyr Gly Thr Gly Ala Asn Glu Ala Thr Asp Glu
                530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Val Pro Gln Ser
                595                 600                 605

Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
                675                 680                 685

Ala Thr Arg Asp Asp Gln Tyr Thr Asn Lys Val Ile Ala Lys Asn Val
                690                 695                 700

Asn Leu Phe Lys Glu Trp Gly Val Thr Ser Phe Glu Leu Pro Pro Gln
705                 710                 715                 720
```

```
Tyr Val Ser Ser Gln Asp Gly Thr Phe Leu Asp Ser Ile Ile Gln Asn
            725                 730                 735
Gly Tyr Ala Phe Glu Asp Arg Tyr Asp Met Ala Met Ser Lys Asn Asn
            740                 745                 750
Lys Tyr Gly Ser Leu Lys Asp Leu Leu Asn Ala Leu Arg Ala Leu His
            755                 760                 765
Ser Val Asn Ile Gln Ala Ile Ala Asp Trp Val Pro Asp Gln Ile Tyr
        770                 775                 780
Asn Leu Pro Gly Lys Glu Val Val Thr Ala Thr Arg Val Asn Asn Tyr
785                 790                 795                 800
Gly Thr Tyr Arg Glu Gly Ala Glu Ile Lys Lys Leu Tyr Val Ala
            805                 810                 815
Asn Ser Lys Thr Asn Glu Thr Asp Phe Gln Gly Lys Tyr Gly Gly Ala
            820                 825                 830
Phe Leu Asp Glu Leu Lys Ala Lys Tyr Pro Glu Ile Phe Glu Arg Val
            835                 840                 845
Gln Ile Ser Asn Gly Gln Lys Met Thr Thr Asp Glu Lys Ile Thr Lys
        850                 855                 860
Trp Ser Ala Lys Tyr Phe Asn Gly Thr Asn Ile Leu Gly Arg Gly Ala
865                 870                 875                 880
Tyr Tyr Val Leu Lys Asp Trp Ala Ser Asn Asp Tyr Leu Thr Asn Arg
            885                 890                 895
Asn Gly Glu Ile Val Leu Pro Lys Gln Leu Val Asn Lys Asn Ser Tyr
            900                 905                 910
Thr Gly Phe Val Ser Asp Ala Asn Gly Thr Lys Phe Tyr Ser Thr Ser
            915                 920                 925
Gly Tyr Gln Ala Lys Asn Ser Phe Ile Gln Asp Glu Asn Gly Asn Trp
        930                 935                 940
Tyr Tyr Phe Asp Lys Arg Gly Tyr Leu Val Thr Gly Ala His Glu Ile
945                 950                 955                 960
Asp Gly Lys His Val Tyr Phe Leu Lys Asn Gly Ile Gln Leu Arg Asp
            965                 970                 975
Ser Ile Arg Glu Asp Glu Asn Gly Asn Gln Tyr Tyr Asp Gln Thr
            980                 985                 990
Gly Ala Gln Val Leu Asn Arg Tyr Tyr Thr Thr Asp Gly Gln Asn Trp
        995                 1000                1005
Arg Tyr Phe Asp Ala Lys Gly Val Met Ala Arg Gly Leu Val Lys
    1010                1015                1020
Ile Gly Asp Gly Gln Gln Phe Phe Asp Glu Asn Gly Tyr Gln Val
    1025                1030                1035
Lys Gly Lys Ile Val Ser Ala Lys Asp Gly Lys Leu Arg Tyr Phe
    1040                1045                1050
Asp Lys Asp Ser Gly Asn Ala Val Ile Asn Arg Phe Ala Gln Gly
    1055                1060                1065
Asp Asn Pro Ser Asp Trp Tyr Tyr Phe Gly Val Glu Phe Ala Lys
    1070                1075                1080
Leu Thr Gly Leu Gln Lys Ile Gly Gln Gln Thr Leu Tyr Phe Asp
    1085                1090                1095
Gln Asp Gly Lys Gln Val Lys Gly Lys Ile Val Thr Leu Ser Asp
    1100                1105                1110
Lys Ser Ile Arg Tyr Phe Asp Ala Asn Ser Gly Glu Met Ala Val
    1115                1120                1125
```

| | | | | | | | | | |
|---|---|---|---|---|---|---|---|---|---|
| Gly | Lys | Phe | Ala | Glu | Gly | Ala | Lys | Asn | Glu | Trp | Tyr | Tyr | Phe | Asp |
| 1130 | | | | | 1135 | | | | | 1140 | | | | |

Gly Lys Phe Ala Glu Gly Ala Lys Asn Glu Trp Tyr Tyr Phe Asp
    1130                1135                1140

Lys Thr Gly Lys Ala Val Thr Gly Leu Gln Lys Ile Gly Lys Gln
    1145                1150                1155

Thr Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asp Ser
    1175                1180                1185

Gly Glu Met Ala Val Gly Lys Phe Ala Glu Gly Ala Lys Asn Glu
    1190                1195                1200

Trp Tyr Tyr Phe Asp Gln Thr Gly Lys Ala Val Thr Gly Leu Gln
    1205                1210                1215

Lys Ile Asp Lys Gln Thr Leu Tyr Phe Asp Gln Asp Gly Lys Gln
    1220                1225                1230

Val Lys Gly Lys Ile Val Thr Leu Ser Asp Lys Ser Ile Arg Tyr
    1235                1240                1245

Phe Asp Ala Asn Ser Gly Glu Met Ala Thr Asn Lys Phe Val Glu
    1250                1255                1260

Gly Ser Gln Asn Glu Trp Tyr Tyr Phe Asp Gln Ala Gly Lys Ala
    1265                1270                1275

Val Thr Gly Leu Gln Gln Val Gly Gln Gln Thr Leu Tyr Phe Thr
    1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
    1310                1315                1320

Lys Trp Ile Gln Leu Glu Asp Gly Ser Trp Met Tyr Phe Asp Arg
    1325                1330                1335

Asp Gly Arg Gly Gln Asn Phe Gly Arg Asn
    1340                1345

<210> SEQ ID NO 3
<211> LENGTH: 3729
<212> TYPE: DNA
<213> ORGANISM: Streptococcus sp. C150

<400> SEQUENCE: 3

```
atgattaacg gtaaagagta ttatgtcgaa gatgacggca cggtccgtaa gaattacgtt      60
ttggaacgta acggcggcag ccaatacttc aatgcagaga ctggtgaact cagcaatcag     120
aaagattatc gcttcgataa gaacggcggc accggtagcg cggcagatag caccactaat     180
accaatgtta ccgtgaatgg tgataagaac gcgttttacg gtaccacgga gaaagacatc     240
gagttggtgg acggttactt cactgcgaac acttggtatc gcccgaaaga aattctgaaa     300
gacggcaagg aatggacggc gagcaccgag aatgataagc gtccgttgct gacggtttgg     360
tggccaagca aggcaatcca ggcgagctat ctgaactata tgcgtgagga gggtctgggt     420
accaaccaaa ccttcacgag ctacagcagc caaacgcaaa tggatcaggc agccttagag     480
gttcaaaaac gtatcgaaga acgcattgca cgcgagggta ataccgattg ctgcgtacc      540
accatcaaga acttcgttaa aacgcagccg ggttggaaca gcacctcaga gaatctggac     600
aactctgacc atctgcaggg tggcgccctg ctgtataaca atagcaaccg cacgtcctac     660
gcgaactctg actatcgctt gctgaatcgt acccctaccc aacaagatgg cacgcgtcgc     720
tacttcaagg acaattcttc tggcggtttc gagttttgc tggcgaatga catcgataac     780
```

```
agcaacccgg cagtgcaggc agaacaactg aattggctgc actacattat gaatattggc    840
agcctgacgg gtggtagcga agatgagaat tcgacggtg ttcgtgttga tgctgtggac     900
aacgttaatg cggacttgct gcaaatcgca tccgactact ttaaagcaaa atacggcgtg    960
gagaaaagcg aagaagaagc gattaagcat ctgtccatct tagaggcgtg gagccacaac   1020
gatgcgtatt acaatgaaga tactaagggc gcacagctgc cgatggatga tccgctgcgc   1080
ttggcgatgg ttttagctt tctgcgtccg attggtaatc gtagcggcct ggagccgttg    1140
atcacgaact cgctgaacga ccgtagcgag agcaaaaaga taccaagcg catggcgaac    1200 tataccttcg tgcgtgctca tgactctgag gtccagagcg ttatcggtca gattatcaag   1260
aacgaaatca atcctcagag cacgggtaac acgttcacgt tggatgaaat gaaaaaggct   1320
tttaagatct ataacgcgga catgcgcagc gcgaataaac gttacaccca atacaacatt   1380
ccgagcgcgt acgcttttat gctgaccaac aaggataccg ttccgcgtgt gtattatggt   1440
gacctgtaca cggacgatgg tcaatacatg gcacagaaat caccgtacca cgatgccatc   1500
agcaccctgc tgcaagcccg tattcgttac gctgctggcg ccaagatat gaagatgagc    1560 tatgtgggca gcggtaatac taacggctgg gacgcgtccg gtgtcctgac cagcgttcgc   1620
tatggtaaag gtgcgaacaa tgcgagcgac gcaggcaccc cgaaacccg caatcaaggc    1680 atggccgtga ttctgagcaa ccagccggca ctgcgtctga atagcaatct gaccatcaac   1740
atgggtgccg cgcatcgtaa tcaagcatat cgcccactgc tgctgaccac gagcaatggc   1800
gtggcgagct acctgaatga cggtgatgcc aacggtattg ttaagtatac cgacgcgaac   1860
ggttatctga cgttcaaccc gggtgagatc agcggcgttc gtaatgctca ggtcgacggt   1920
tatttggcgg tttgggtccc gctgggcgca agcgagaacc aagacgtgcg tgttgccgcg   1980
agcaaaagca aaacagcag cggtctggta tacgactcta gcgcggcact ggactcccaa    2040
gttatctatg aaggctttag caattttcag gatttcgtgc aggacccgtc ccagtatacc   2100
aacaagaaaa tcgccgagaa tgcaaatttg ttcaaatcct ggggcattac ctcgtttgaa   2160
tttgccccgc agtacgtgag ctccgacgat ggtaccttcc tggacagcgt cattcagaac   2220
ggctacgcgt tcagcgatcg ctacgatatt ggtatgagca agacaacaa gtacggcagc    2280 ctggcagatc tgaaagcggc gcttaagtcc ctgcacgccg tcggtatctc cgcgatcgca   2340
gactgggtcc cggaccagat ttacaatctg cctggtgatg aagtggtgac cgccacccgt   2400
gtgaacaatt acggtgaaac gaaagacggc gcgatcatcg accacagcct gtacgtcgcg   2460
aaaacccgca cgtttggtaa cgattatcaa ggtaagtacg gtggcgctta cctggatgaa   2520
ctcaagcgtc tgtatccgca gttttcgac cgtgttcaga tcagcaccgg caagcgtctg    2580
accaccgatg agaagattac gaagtggtcc gcgaaataca tgaatggtac caacattctg   2640
gaccgtggta gcgagtatgt tctgaagaac ggcctgtcgg gttactatgg cacgaacggt   2700
ggcaaagttt ccctgccgaa agtcgtcggc tctaaccaga gcacgaacaa caataaccaa   2760
aacggtgatg cagcggccg tttcgagaaa agctggggta gcgtgtatta tcgttacaat   2820
gacggccagc gtgcgcgtaa tgctttcatt aaagacaacg atggtaacgt ttactacttt   2880
gacaacactg gccgtatggc catcggtgaa aagacgattg atggtaagca gtacttcttc   2940
ctggcgaacg gtgttcagct gcgtgacggt taccgtcaga accgtcgcgg tcaggtcttt   3000
tactacgacg agaacggtat tatgagccag acgggtaagc cgtccccgaa gccagagcca   3060
aaaccggaca caatacgtt ttctcgcaat caattcattc agattggcaa taacgtctgg    3120
gcctattacg atggtaatgg taaaagagtg atcggtcgtc agaatatcaa tggtcaagaa   3180
```

-continued

```
ctgttttcg ataacaacgg cgtccaagtc aagggtcgca ccgcccaagt ggacggcgtg    3240
acccgttact ttgacgctaa ttctggcgag atggcgcgta accgcttcgc agaagtggag    3300
ccgggtgtct gggcttactt caacaacgat ggtgccgcgg tgaccggtag ccagaacatt    3360
aatggccaga ccctgtattt cgaccagaat ggtcaccaag ttaaaggtgc cctggttacc    3420
gtcgatggca atctgcgcta ttacgacgcg aattcgggcg acctgtatcg caaccgcttc    3480
caagaagtca atggcagctg gtactatttt gatggtaacg gtaacgcagt caaaggcatg    3540
gtgaacatta acggtcagaa tctgctgttt gataatgatg gcaaacaagt gaaaggtcac    3600
ctggtccgcg ttaatggtgt cattcgttat tacgacccga atagcggtga gatggctgtt    3660
aatcgttggg tcgagatcag cagcggttgg tgggtgtact tgatggcga gggtcgtggt    3720 caaatctaa                                                            3729
```

<210> SEQ ID NO 4
<211> LENGTH: 1242
<212> TYPE: PRT
<213> ORGANISM: Streptococcus sp. C150

<400> SEQUENCE: 4

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
        195                 200                 205

Ala Leu Leu Tyr Asn Asn Ser Asn Arg Thr Ser Tyr Ala Asn Ser Asp
    210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270
```

```
Leu His Tyr Ile Met Asn Ile Gly Ser Leu Thr Gly Gly Ser Glu Asp
            275                 280                 285

Glu Asn Phe Asp Gly Val Arg Val Asp Ala Val Asp Asn Val Asn Ala
    290                 295                 300

Asp Leu Leu Gln Ile Ala Ser Asp Tyr Phe Lys Ala Lys Tyr Gly Val
305                 310                 315                 320

Glu Lys Ser Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
                340                 345                 350

Leu Pro Met Asp Asp Pro Leu Arg Leu Ala Met Val Phe Ser Phe Leu
            355                 360                 365

Arg Pro Ile Gly Asn Arg Ser Gly Leu Glu Pro Leu Ile Thr Asn Ser
    370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
    435                 440                 445

Arg Ser Ala Asn Lys Arg Tyr Thr Gln Tyr Asn Ile Pro Ser Ala Tyr
450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
                485                 490                 495

His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
    515                 520                 525

Gly Trp Asp Ala Ser Gly Val Leu Thr Ser Val Arg Tyr Gly Lys Gly
530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
    595                 600                 605

Asp Ala Asn Gly Ile Val Lys Tyr Thr Asp Ala Asn Gly Tyr Leu Thr
610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
    675                 680                 685
```

```
Phe Gln Asp Phe Val Gln Asp Pro Ser Gln Tyr Thr Asn Lys Lys Ile
690                 695                 700
Ala Glu Asn Ala Asn Leu Phe Lys Ser Trp Gly Ile Thr Ser Phe Glu
705                 710                 715                 720
Phe Ala Pro Gln Tyr Val Ser Ser Asp Asp Gly Thr Phe Leu Asp Ser
            725                 730                 735
Val Ile Gln Asn Gly Tyr Ala Phe Ser Asp Arg Tyr Asp Ile Gly Met
            740                 745                 750
Ser Lys Asp Asn Lys Tyr Gly Ser Leu Ala Asp Leu Lys Ala Ala Leu
            755                 760                 765
Lys Ser Leu His Ala Val Gly Ile Ser Ala Ile Ala Asp Trp Val Pro
770                 775                 780
Asp Gln Ile Tyr Asn Leu Pro Gly Asp Glu Val Val Thr Ala Thr Arg
785                 790                 795                 800
Val Asn Asn Tyr Gly Glu Thr Lys Asp Gly Ala Ile Ile Asp His Ser
                805                 810                 815
Leu Tyr Val Ala Lys Thr Arg Thr Phe Gly Asn Asp Tyr Gln Gly Lys
            820                 825                 830
Tyr Gly Gly Ala Tyr Leu Asp Glu Leu Lys Arg Leu Tyr Pro Gln Phe
835                 840                 845
Phe Asp Arg Val Gln Ile Ser Thr Gly Lys Arg Leu Thr Thr Asp Glu
850                 855                 860
Lys Ile Thr Lys Trp Ser Ala Lys Tyr Met Asn Gly Thr Asn Ile Leu
865                 870                 875                 880
Asp Arg Gly Ser Glu Tyr Val Leu Lys Asn Gly Leu Ser Gly Tyr Tyr
            885                 890                 895
Gly Thr Asn Gly Gly Lys Val Ser Leu Pro Lys Val Val Gly Ser Asn
            900                 905                 910
Gln Ser Thr Asn Asn Asn Gln Asn Gly Asp Gly Ser Gly Arg Phe
            915                 920                 925
Glu Lys Ser Trp Gly Ser Val Tyr Tyr Arg Tyr Asn Asp Gly Gln Arg
930                 935                 940
Ala Arg Asn Ala Phe Ile Lys Asp Asn Asp Gly Asn Val Tyr Tyr Phe
945                 950                 955                 960
Asp Asn Thr Gly Arg Met Ala Ile Gly Glu Lys Thr Ile Asp Gly Lys
            965                 970                 975
Gln Tyr Phe Phe Leu Ala Asn Gly Val Gln Leu Arg Asp Gly Tyr Arg
            980                 985                 990
Gln Asn Arg Arg Gly Gln Val Phe  Tyr Tyr Asp Glu Asn  Gly Ile Met
            995                 1000                1005
Ser Gln Thr Gly Lys Pro Ser  Pro Lys Pro Glu Pro  Lys Pro Asp
    1010                1015                1020
Asn Asn Thr Phe Ser Arg Asn  Gln Phe Ile Gln Ile  Gly Asn Asn
    1025                1030                1035
Val Trp Ala Tyr Tyr Asp Gly  Asn Gly Lys Arg Val  Ile Gly Arg
    1040                1045                1050
Gln Asn Ile Asn Gly Gln Glu  Leu Phe Phe Asp Asn  Asn Gly Val
    1055                1060                1065
Gln Val Lys Gly Arg Thr Ala  Gln Val Asp Gly Val  Thr Arg Tyr
    1070                1075                1080
Phe Asp Ala Asn Ser Gly Glu  Met Ala Arg Asn Arg  Phe Ala Glu
    1085                1090                1095
Val Glu Pro Gly Val Trp Ala  Tyr Phe Asn Asn Asp  Gly Ala Ala
```

```
       1100                1105                1110
Val Thr Gly Ser Gln Asn Ile Asn Gly Gln Thr Leu Tyr Phe Asp
       1115                1120                1125

Gln Asn Gly His Gln Val Lys Gly Ala Leu Val Thr Val Asp Gly
       1130                1135                1140

Asn Leu Arg Tyr Tyr Asp Ala Asn Ser Gly Asp Leu Tyr Arg Asn
       1145                1150                1155

Arg Phe Gln Glu Val Asn Gly Ser Trp Tyr Tyr Phe Asp Gly Asn
       1160                1165                1170

Gly Asn Ala Val Lys Gly Met Val Asn Ile Asn Gly Gln Asn Leu
       1175                1180                1185

Leu Phe Asp Asn Asp Gly Lys Gln Val Lys Gly His Leu Val Arg
       1190                1195                1200

Val Asn Gly Val Ile Arg Tyr Tyr Asp Pro Asn Ser Gly Glu Met
       1205                1210                1215

Ala Val Asn Arg Trp Val Glu Ile Ser Ser Gly Trp Trp Val Tyr
       1220                1225                1230

Phe Asp Gly Glu Gly Arg Gly Gln Ile
       1235                1240

<210> SEQ ID NO 5
<211> LENGTH: 3942
<212> TYPE: DNA
<213> ORGANISM: Streptococcus mutans

<400> SEQUENCE: 5
atgattgacg gcaaatacta ctactatgac aacaacggca agtacgcac caatttcacg       60 ttgatcgcgg acggtaaaat cctgcatttt gatgaaactg cgcgtacac cgacactagc      120 attgataccg tgaacaagga tattgtcacg acgcgtagca acctgtataa gaaatacaat      180
caagtgtatg atcgcagcgc gcagagcttc gagcatgttg atcactacct gacggcggaa      240
tcttggtacc gtccgaaata cattctgaaa gatggcaaga cctggaccca gagcaccgag      300
aaggacttcc gtcctctgct gatgacctgg tggccgagcc aggaaacgca gcgccagtat      360
gtcaacttca tgaacgccca gttgggtatc aacaaaacgt acgacgacac cagcaatcag      420
ctgcaattga acatcgctgc tgcaacgatc aagcaaaga tcgaagccaa atcacgacg       480 ctgaagaaca ccgattggct gcgtcaaacg atcagcgcgt cgtcaaaac ccaaagcgct      540 tggaatagcg acagcgaaaa gccgtttgat gaccatctgc aaaacggtgc ggttctgtat      600
gataacgaag gtaaattgac gccgtatgcc aatagcaact atcgtattct gaaccgcacg      660
ccgaccaacc agaccggtaa gaaggacccg cgttataccg ccgacaacac gatcggcggc      720
tacgagtttc tgctggccaa cgacgtggat aatagcaacc cggtggttca ggccgagcag      780
ctgaactggc tgcacttcct gatgaacttt ggtaatatct acgcaaacga ccctgacgct      840
aacttcgact ccatccgcgt tgacgctgtc gataatgtgg acgccgatct gttacagatc      900
gcgggtgact atctgaaagc ggcaaagggc atccataaga tgacaaagc ggcgaacgac       960 cacctgtcca ttctggaagc gtggagcgac aatgacactc cgtatctgca tgatgatggc     1020
gacaacatga ttaacatgga taacaaactg cgcctgagcc tgctgttctc cctggcgaaa     1080
ccgctgaatc agcgtagcgg tatgaacccg ttgattacga cagcctggt caaccgtact     1140 gatgataatg ccgaaacggc ggcagtgcca agctactctt ttatccgtgc ccacgatagc     1200
gaggtccagg atttgattcg tgatatcatt aaggctgaga ttaacccgaa cgtcgtcggt     1260
```

```
tacagcttca cgatggaaga gattaagaag gcatttgaga tctacaataa ggacctgttg    1320
gccacggaga agaagtatac ccactataac accgcattga gctacgcgtt gctgctgacg    1380
aacaagagca gcgtgccgcg tgtctactat ggtgatatgt ttacggacga tggtcaatac    1440
atggcccaca agaccattaa ctacgaggca atcgaaaccc tgctgaaagc acgtatcaag    1500
tacgtgtccg gtggtcaggc tatgcgcaac cagcaagtgg gtaattcgga gatcatcacc    1560
agcgtgcgtt acggtaaagg tgcgctgaag gcgatggata cgggtgaccg cactacccgt    1620
acctctggtg tggcggtcat tgagggcaac aacccgagct tgcgcctgaa ggcttctgat    1680
cgtgtggttg tgaatatggg tgcggcccac aaaaatcaag cctatcgccc gctgctgttg    1740
acgaccgata acggcattaa ggcctatcac agcgaccaag aagcggcagg cctggtgcgt    1800
tacaccaacg accgtggcga actgatcttt accgcagccg acattaaggg ctacgcaaat    1860
ccgcaagtta gcggctacct gggcgtctgg gtccctgttg gcgcagcagc tgatcaggac    1920
gttcgtgttg cggcgagcac cgcgccaagc acggacggca agagcgttca ccagaacgcg    1980
gctctggaca gccgtgtgat gttcgagggt ttctcgaact tccaggcatt tgctaccaag    2040
aaagaagagt ataccaatgt ggtcatcgct aagaatgtgg ataagttcgc ggagtggggt    2100
gtcaccgatt tcgagatggc tccgcaatac gtttctagca ccgacggtag cttttttggat   2160
agcgtgattc aaaacggtta tgcttttacc gaccgttacg acctgggcat cagcaagccg    2220
aacaaatatg gcaccgcgga cgatctggtt aaagcgatta aggcattgca cagcaaaggc    2280
atcaaagtta tggcggattg ggttccggac cagatgtatg ccctgccgga aaaagaggtt    2340
gtgacggcaa cccgtgttga caaatacggt acgccggtag ctggcagcca gatcaaaaac    2400
acgctgtacg tggtcgatgg taaatctagc ggtaaggacc agcaggcgaa gtacggtggt    2460
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc aaccaacacc     2640
tactttaaca tcagcgacaa taaagagatc aatttcctgc aaagacgttt gctgaaccag    2700
gattctcaag ttggctttag ctacgacggt aagggctatg tgtactacag cacctcgggc    2760
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa aatgaggacg gtacgtacgc gtattatggc    2940
aatgatggtc gccgctacga gaatggctat tatcagtttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc    3180
aaatggctgt acctgggtga ggacggcgcg gcagtcaccg tagccagac gatcaatggt    3240
cagcacctgt attttcgtgc taacggcgtt caggttaagg gtgagttcgt gaccgatcgt    3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc gcgcgaacg gtgttcaggt aaaaggtgag    3480
tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
```

```
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg gttacgcggt gaccggtgcc cgcacgatta atggtcaaca cttgtacttc    3840
cgtgccaacg tgtccaggt gaagggtgaa tttgtgaccg accgctatgg tcgcatttct    3900
tactacgacg caaattccgg tgaacgcgtc cgtatcaatt aa    3942

<210> SEQ ID NO 6
<211> LENGTH: 1313
<212> TYPE: PRT
<213> ORGANISM: Streptococcus mutans

<400> SEQUENCE: 6
```

Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
    210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
        275                 280                 285

Ala Val Asp Asn Val Asp Ala Asp Leu Leu Gln Ile Ala Gly Asp Tyr
    290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
            325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
            355                 360                 365

Asn Pro Leu Ile Thr Asn Ser Leu Val Asn Arg Thr Asp Asp Asn Ala
370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
            405                 410                 415

Asn Val Val Gly Tyr Ser Phe Thr Met Glu Glu Ile Lys Lys Ala Phe
            420                 425                 430

Glu Ile Tyr Asn Lys Asp Leu Leu Ala Thr Glu Lys Lys Tyr Thr His
            435                 440                 445

Tyr Asn Thr Ala Leu Ser Tyr Ala Leu Leu Thr Asn Lys Ser Ser
450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
            485                 490                 495

Ala Arg Ile Lys Tyr Val Ser Gly Gly Gln Ala Met Arg Asn Gln Gln
            500                 505                 510

Val Gly Asn Ser Glu Ile Ile Thr Ser Val Arg Tyr Gly Lys Gly Ala
            515                 520                 525

Leu Lys Ala Met Asp Thr Gly Asp Arg Thr Thr Arg Thr Ser Gly Val
            530                 535                 540

Ala Val Ile Glu Gly Asn Asn Pro Ser Leu Arg Leu Lys Ala Ser Asp
545                 550                 555                 560

Arg Val Val Val Asn Met Gly Ala Ala His Lys Asn Gln Ala Tyr Arg
            565                 570                 575

Pro Leu Leu Leu Thr Thr Asp Asn Gly Ile Lys Ala Tyr His Ser Asp
            580                 585                 590

Gln Glu Ala Ala Gly Leu Val Arg Tyr Thr Asn Asp Arg Gly Glu Leu
            595                 600                 605

Ile Phe Thr Ala Ala Asp Ile Lys Gly Tyr Ala Asn Pro Gln Val Ser
            610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
            645                 650                 655

His Gln Asn Ala Ala Leu Asp Ser Arg Val Met Phe Glu Gly Phe Ser
            660                 665                 670

Asn Phe Gln Ala Phe Ala Thr Lys Lys Glu Tyr Thr Asn Val Val
            675                 680                 685

Ile Ala Lys Asn Val Asp Lys Phe Ala Glu Trp Gly Val Thr Asp Phe
            690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
            725                 730                 735

Ile Ser Lys Pro Asn Lys Tyr Gly Thr Ala Asp Asp Leu Val Lys Ala

-continued

```
            740                 745                 750
Ile Lys Ala Leu His Ser Lys Gly Ile Lys Val Met Ala Asp Trp Val
            755                 760                 765
Pro Asp Gln Met Tyr Ala Leu Pro Glu Lys Glu Val Val Thr Ala Thr
            770                 775             780
Arg Val Asp Lys Tyr Gly Thr Pro Val Ala Gly Ser Gln Ile Lys Asn
785             790                 795                 800
Thr Leu Tyr Val Val Asp Gly Lys Ser Ser Gly Lys Asp Gln Gln Ala
                    805                 810                 815
Lys Tyr Gly Gly Ala Phe Leu Glu Glu Leu Gln Ala Lys Tyr Pro Glu
                820                 825                 830
Leu Phe Ala Arg Lys Gln Ile Ser Thr Gly Val Pro Met Asp Pro Ser
            835                 840                 845
Val Lys Ile Lys Gln Trp Ser Ala Lys Tyr Phe Asn Gly Thr Asn Ile
        850                 855                 860
Leu Gly Arg Gly Ala Gly Tyr Val Leu Lys Asp Gln Ala Thr Asn Thr
865                 870                 875                 880
Tyr Phe Asn Ile Ser Asp Asn Lys Glu Ile Asn Phe Leu Pro Lys Thr
                    885                 890                 895
Leu Leu Asn Gln Asp Ser Gln Val Gly Phe Ser Tyr Asp Gly Lys Gly
                900                 905                 910
Tyr Val Tyr Tyr Ser Thr Ser Gly Tyr Gln Ala Lys Asn Thr Phe Ile
            915                 920                 925
Ser Glu Gly Asp Lys Trp Tyr Tyr Phe Asp Asn Asn Gly Tyr Met Val
        930                 935                 940
Thr Gly Ala Gln Ser Ile Asn Gly Val Asn Tyr Tyr Phe Leu Pro Asn
945                 950                 955                 960
Gly Leu Gln Leu Arg Asp Ala Ile Leu Lys Asn Glu Asp Gly Thr Tyr
                    965                 970                 975
Ala Tyr Tyr Gly Asn Asp Gly Arg Arg Tyr Glu Asn Gly Tyr Tyr Gln
                980                 985                 990
Phe Met Ser Gly Val Trp Arg His  Phe Asn Asn Gly Glu  Met Ser Val
            995                 1000                1005
Gly Leu  Thr Val Ile Asp Gly  Gln Val Gln Tyr Phe  Asp Glu Met
    1010                1015                1020
Gly Tyr  Gln Ala Lys Gly Lys  Phe Val Thr Thr Ala  Asp Gly Lys
    1025                1030                1035
Ile Arg  Tyr Phe Asp Lys Gln  Ser Gly Asn Met Tyr  Arg Asn Arg
    1040                1045                1050
Phe Ile  Glu Asn Glu Glu Gly  Lys Trp Leu Tyr Leu  Gly Glu Asp
    1055                1060                1065
Gly Ala  Ala Val Thr Gly Ser  Gln Thr Ile Asn Gly  Gln His Leu
    1070                1075                1080
Tyr Phe  Arg Ala Asn Gly Val  Gln Val Lys Gly Glu  Phe Val Thr
    1085                1090                1095
Asp Arg  His Gly Arg Ile Ser  Tyr Tyr Asp Gly Asn  Ser Gly Asp
    1100                1105                1110
Gln Ile  Arg Asn Arg Phe Val  Arg Asn Ala Gln Gly  Gln Trp Phe
    1115                1120                1125
Tyr Phe  Asp Asn Asn Gly Tyr  Ala Val Thr Gly Ala  Arg Thr Ile
    1130                1135                1140
Asn Gly  Gln His Leu Tyr Phe  Arg Ala Asn Gly Val  Gln Val Lys
    1145                1150                1155
```

Gly Glu Phe Val Thr Asp Arg His Gly Arg Ile Ser Tyr Tyr Asp
    1160                1165                1170

Gly Asn Ser Gly Asp Gln Ile Arg Asn Arg Phe Val Arg Asn Ala
    1175                1180                1185

Gln Gly Gln Trp Phe Tyr Phe Asp Asn Asn Gly Tyr Ala Val Thr
    1190                1195                1200

Gly Ala Arg Thr Ile Asn Gly Gln His Leu Tyr Phe Arg Ala Asn
    1205                1210                1215

Gly Val Gln Val Lys Gly Glu Phe Val Thr Asp Arg Tyr Gly Arg
    1220                1225                1230

Ile Ser Tyr Tyr Asp Gly Asn Ser Gly Asp Gln Ile Arg Asn Arg
    1235                1240                1245

Phe Val Arg Asn Ala Gln Gly Gln Trp Phe Tyr Phe Asp Asn Asn
    1250                1255                1260

Gly Tyr Ala Val Thr Gly Ala Arg Thr Ile Asn Gly Gln His Leu
    1265                1270                1275

Tyr Phe Arg Ala Asn Gly Val Gln Val Lys Gly Glu Phe Val Thr
    1280                1285                1290

Asp Arg Tyr Gly Arg Ile Ser Tyr Tyr Asp Ala Asn Ser Gly Glu
    1295                1300                1305

Arg Val Arg Ile Asn
    1310

<210> SEQ ID NO 7
<211> LENGTH: 4047
<212> TYPE: DNA
<213> ORGANISM: Streptococcus sanguinis

<400> SEQUENCE: 7
atgattgatg gtaaaaagta ttacgtacag gacgacggca cggttaagaa gaatttcgcg     60
gttgagctga atggcaagat cctgtacttc gatgcagaga ctggtgcgtt gattgacagc    120
gcggagtatc aattccaaca aggcaccagc agcctgaata atgagttcac tcaaaagaac    180
gccttttacg gtacgaccga taaggatgtg gaaaccattg atggttactt gaccgccgat    240
tcctggtatc gtccgaagtt cattctgaaa gatggcaaaa cctggacggc gagcacggaa    300
attgacttgc gtccgttgtt gatggcgtgg tggccggaca acagaccca ggttagctac    360 ctgaattaca tgaaccagca aggcttgggt gcaggcgcct tcgaaaacaa agtagagcag    420
gcaattctga ccggtgcgtc caacaggta caacgtaaaa tcgaagaacg catcggtaaa    480
gagggtgata ccaagtggct gcgtaccctg atgggtgcat ttgtaaagac ccagccgaac    540
tggaacatta agaccgagtc cgaaaccact ggcacgaata agatcatctc gcaaggtggc    600
gcactgctgt atagcaattc gacaagacg agccatgcca actctaagta ccgtatcctg    660
aaccgcaccc cgaccaacca aacgggcacg ccgaaatact ttattgacaa gagcaatggt    720
ggttatgaat ttctgctggc gaatgacttt gacaatagca atccggcagt gcaagcggaa    780
cagctgaact ggttgcactt tatgatgaat tttggctcca tcgttgcaaa tgatccgacg    840
gccaacttcg acggcgtccg cgttgacgct gtggataacg tgaatgcgga tctgttgcaa    900
attgcgagcg actattttcaa gagccgctat aaagtcggcg aaagcgaaga gaggccatt    960 aagcaccctgt ccatcctgga agcgtggagc gacaacgacc cggactacaa caaggatact   1020
aaaggtgccc aactgccgat cgacaacaaa ctgcgtctga gctgctgta ctccttcatg   1080 cgtaagctga gcatccgtag cggcgtcgag ccgaccatca ccaactctct gaatgatcgc   1140

```
agcacggaga agaagaatgg tgagcgtatg gcaaactata tcttcgttcg tgcacatgat    1200
agcgaggtgc aaacggtcat cgccgacatt atccgtgaga acatcaatcc gaataccgac    1260
ggcctgacgt tcacgatgga tgaactgaag caggccttta aaatttacaa tgaggatatg    1320
cgtaaagccg acaaaaagta cacgcagttc aatatcccga ccgcgcacgc gctgatgctg    1380
agcaacaaag attctatcac ccgcgtttac tacggtgacc tgtatacgga tgacggtcag    1440
tatatggaaa agaaaagccc gtatcacgac gccattgacg ctctgctgcg tgcgcgtatc    1500
aaatatgttg cgggtggtca ggacatgaag gtgacctata tgggcgtgcc gcgtgaggca    1560
gataaatgga gctataacgg catcctgacc agcgttcgtt atggtacggg tgccaacgag    1620
gcaaccgacg agggtacggc agaaacccgt acccagggca tggccgtcat tgccagcaac    1680
aatccgaacc tgaaactgaa cgagtgggac aagttgcagg tcaacatggg tgcagctcac    1740
aaaaaccaat actatcgtcc ggtgctgctg accaccaagg acggcatctc gcgctacctg    1800
accgacgaag aagtcccgca gagcctgtgg aaaaagaccg atgcgaacgg catcttgacg    1860
tttgacatga atgatattgc gggttacagc aacgtccaag tgagcggtta tctggccgtc    1920
tgggttcctg tgggtgcgaa ggcggaccag gacgctcgtg ttacggcatc taagaagaaa    1980
aatgcctctg gccaagttta cgaaagcagc gcagccctgg actcccagct gatctatgag    2040
ggcttcagca atttttcagga cttttgccacc cgtgacgacc agtacactaa caaggttatc    2100
gcgaaaaacg tcaatctgtt taaagagtgg ggcgtcacca gcttcgaatt gccgccacag    2160
tatgtgagca gccaagacgg tacgttcctg gatagcatca tccagaatgg ttatgcattc    2220
gaagatcgct atgatatggc gatgagcaaa aacaataagt acggtagctt gaacgacctg    2280
ttgaacgcct tgcgtgcact gcatagcgtg aatatccaag cgattgcgga ttgggtgccg    2340
gaccagattt acaatctgcc gggtaaagaa gttgtcactg caacccgtgt taacaattat    2400
ggcacgtatc gtgagggtag cgagattaaa gagaacctgt acgttgctaa caccaaaaacc    2460 aatggtacgg actaccaagg taagtatggt ggtgcgttct tggacgagct gaaagccaaa    2520 tacccctgaga ttttttgagcg cgtccaaatc agcaacggcc agaagatgac caccgacgag    2580
aagattacga aatggtccgc caaacacttt aacggcacga acattctggg tcgtggtgcg    2640
tattatgtgc tgaaagactg ggcgagcaac gagtacctga ataacaaaaa tggcgagatg    2700
gttctgccga agcagctggt taataaaaat gcatataccg gcttcgtcag cgacgcgagc    2760
ggcaccaaat actattctac cagcggctat caggctcgta atagctttat tcaagatgaa    2820
aatggtaatt ggtactactt caataaccgt ggttatttgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
tacactacgg acggccaaaa ttggcgctac ttcgacgtta aaggcgtcat ggcccgtggt    3060
ctggtcacga tgggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgg ttacgggcct gcaaaaggtt ggtcagcaaa ctctgtactt tgatcaggac    3300
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
```

```
tatttcgacc aggatggtaa acaagtcaaa ggtaaggtgg tcacgctggc tgataagtct      3540
atccgctact tcgacgcgaa cagcggtgag atggcagtgg gcaaattcgc cgaaggcgca      3600
aagaatgagt ggtattactt tgaccaggcg ggcaaggctg ttaccggtct gcaaaagatc      3660
ggccaacaga cgctgtattt cgaccagaac ggtaaacagg ttaagggtaa agtggtcacc      3720
ctggcggata agagcatccg ctatttcgac gctaactctg gcgaaatggc aagcaataag      3780
ttcgttgagg gtgccaaaaa tgaatggtac tatttcgatc aggctggcaa ggcagtgacg      3840
ggtctgcaac aaattggcca gcagaccctg tattttgacc agaatggcaa acaggtgaag      3900
ggtaagattg tgtatgttaa tggtgcgaat cgctactttg atgccaatag cggtgaaatg      3960
gcgcgtaaca agtggattca gctggaagat ggcagctgga tgtattttga ccgcaatggt      4020
cgtggtcgtc gtttcggttg gaactaa                                         4047
```

<210> SEQ ID NO 8
<211> LENGTH: 1348
<212> TYPE: PRT
<213> ORGANISM: Streptococcus sanguinis

<400> SEQUENCE: 8

```
Met Ile Asp Gly Lys Lys Tyr Tyr Val Gln Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270
```

-continued

Ser Ile Val Ala Asn Asp Pro Thr Ala Asn Phe Asp Gly Val Arg Val
    275                 280                 285

Asp Ala Val Asp Asn Val Asn Ala Asp Leu Leu Gln Ile Ala Ser Asp
290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365

Val Glu Pro Thr Ile Thr Asn Ser Leu Asn Asp Arg Ser Thr Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
        675                 680                 685

Ala Thr Arg Asp Asp Gln Tyr Thr Asn Lys Val Ile Ala Lys Asn Val

-continued

```
            690             695             700
Asn Leu Phe Lys Glu Trp Gly Val Thr Ser Phe Glu Leu Pro Pro Gln
705             710             715             720

Tyr Val Ser Ser Gln Asp Gly Thr Phe Leu Asp Ser Ile Ile Gln Asn
            725             730             735

Gly Tyr Ala Phe Glu Asp Arg Tyr Asp Met Ala Met Ser Lys Asn Asn
            740             745             750

Lys Tyr Gly Ser Leu Asn Asp Leu Leu Asn Ala Leu Arg Ala Leu His
        755             760             765

Ser Val Asn Ile Gln Ala Ile Ala Asp Trp Val Pro Asp Gln Ile Tyr
770             775             780

Asn Leu Pro Gly Lys Glu Val Val Thr Ala Thr Arg Val Asn Asn Tyr
785             790             795             800

Gly Thr Tyr Arg Glu Gly Ser Glu Ile Lys Glu Asn Leu Tyr Val Ala
            805             810             815

Asn Thr Lys Thr Asn Gly Thr Asp Tyr Gln Gly Lys Tyr Gly Gly Ala
            820             825             830

Phe Leu Asp Glu Leu Lys Ala Lys Tyr Pro Glu Ile Phe Glu Arg Val
        835             840             845

Gln Ile Ser Asn Gly Gln Lys Met Thr Thr Asp Glu Lys Ile Thr Lys
850             855             860

Trp Ser Ala Lys His Phe Asn Gly Thr Asn Ile Leu Gly Arg Gly Ala
865             870             875             880

Tyr Tyr Val Leu Lys Asp Trp Ala Ser Asn Glu Tyr Leu Asn Asn Lys
            885             890             895

Asn Gly Glu Met Val Leu Pro Lys Gln Leu Val Asn Lys Asn Ala Tyr
            900             905             910

Thr Gly Phe Val Ser Asp Ala Ser Gly Thr Lys Tyr Tyr Ser Thr Ser
        915             920             925

Gly Tyr Gln Ala Arg Asn Ser Phe Ile Gln Asp Glu Asn Gly Asn Trp
930             935             940

Tyr Tyr Phe Asn Asn Arg Gly Tyr Leu Val Thr Gly Ala Gln Glu Ile
945             950             955             960

Asp Gly Lys Gln Leu Tyr Phe Leu Lys Asn Gly Ile Gln Leu Arg Asp
            965             970             975

Ser Leu Arg Glu Asp Glu Asn Gly Asn Gln Tyr Tyr Asp Lys Thr
        980             985             990

Gly Ala Gln Val Leu Asn Arg Tyr Tyr Thr Thr Asp Gly Gln Asn Trp
            995             1000            1005

Arg Tyr Phe Asp Val Lys Gly Val Met Ala Arg Gly Leu Val Thr
    1010            1015            1020

Met Gly Gly Asn Gln Gln Phe Phe Asp Gln Asn Gly Tyr Gln Val
    1025            1030            1035

Lys Gly Lys Ile Ala Arg Ala Lys Asp Gly Lys Leu Arg Tyr Phe
    1040            1045            1050

Asp Lys Asp Ser Gly Asn Ala Ala Ala Asn Arg Phe Ala Gln Gly
    1055            1060            1065

Asp Asn Pro Ser Asp Trp Tyr Tyr Phe Gly Ala Asp Gly Val Ala
    1070            1075            1080

Val Thr Gly Leu Gln Lys Val Gly Gln Gln Thr Leu Tyr Phe Asp
    1085            1090            1095

Gln Asp Gly Lys Gln Val Lys Gly Lys Val Val Thr Leu Ala Asp
    1100            1105            1110
```

```
Lys Ser Ile Arg Tyr Phe Asp Ala Asn Ser Gly Glu Met Ala Val
    1115                1120                1125

Asn Lys Phe Val Glu Gly Ala Lys Asn Val Trp Tyr Tyr Phe Asp
    1130                1135                1140

Gln Ala Gly Lys Ala Val Thr Gly Leu Gln Thr Ile Asn Lys Gln
    1145                1150                1155

Val Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
    1190                1195                1200

Trp Tyr Tyr Phe Asp Gln Ala Gly Lys Ala Val Thr Gly Leu Gln
    1205                1210                1215

Lys Ile Gly Gln Gln Thr Leu Tyr Phe Asp Gln Asn Gly Lys Gln
    1220                1225                1230

Val Lys Gly Lys Val Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 9
<211> LENGTH: 3744
<212> TYPE: DNA
<213> ORGANISM: Streptococcus salivarius

<400> SEQUENCE: 9
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaagacggg caagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aaccggggttg aacagcacc     600 tctgaaaatc tggacaataa tgatcatctg caaggtggcg ccctgctgta caataacgac     660
```

| | |
|---|---|
| tcccgcacga gccacgcgaa cagcgactat cgcctgctga atcgtacgcc gaccagccag | 720 |
| accggcaaac acaatccgaa ataccaccaaa gataccagca atggtggttt cgaatttctg | 780 |
| ctggcgaacg acatcgataa ctctaatccg gcggttcaag cagagcaact gaactggctg | 840 |
| cattacatta tgaacatcgg taccatcacg ggcggttctg aggatgaaaa cttcgacggc | 900 |
| gttcgtgttg acgctgtgga taatgtgaat gcggatctgc tgcaaatcgc gagcgactat | 960 |
| ttcaaagcaa atacggtgc tgatcaaagc caagatcagg cgatcaaaca cttgagcatc | 1020 |
| ctggaagcgt ggtcccataa cgacgcctac tataacgaag ataccaaagg cgcgcagttg | 1080 |
| ccgatggatg atccgatgca cctggctctg gtctactcgc tgctgcgtcc gatcggcaat | 1140 |
| cgcagcggtg tggaaccgct gatttccaac agcctgaatg accgtagcga gtccggtaag | 1200 |
| aacagcaaac gtatggcgaa ctacgcgttc gtacgcgcgc atgatagcga ggtgcaatcg | 1260 |
| attattggcc agatcatcaa aaacgagatc aatccgcaaa gcaccggtaa tacgttcacc | 1320 |
| ctggatgaga tgaagaaagc gtttgagatt tacaacaagg atatgcgtag cgcgaataag | 1380 |
| cagtatacgc agtacaacat cccgagcgcg tatgcgttga tgctgaccca caaggatacc | 1440 |
| gttccgcgtg tgtattacgg tgatatgtat acggacgacg gtcagtacat ggcgcaaaag | 1500 |
| agcccatact atgatgcgat cgaaacgctg ctgaaaggtc gcatccgcta tgccgcaggt | 1560 |
| ggtcaggaca tgaaggtcaa ctatattggt tacggtaaca ctaacggctg ggatgctgcg | 1620 |
| ggcgtgctga ccagcgtacg ttatggcacg ggcgcaaata cgccagcga tacgggtacc | 1680 |
| gccgaaacgc gtaatcaagg tatggcagtg attgttagca accaaccggc gctgcgtctg | 1740 |
| actagcaatt tgaccattaa catgggtgcc gcacaccgta atcaggctta ccgtccgctg | 1800 |
| ctgctgacga ccaacgatgg cgtcgcgacc tatttgaacg atagcgatgc gaatggtatc | 1860 |
| gttaagtaca ccgacggtaa tggtaatctg accttctccg caaacgagat tcgtggcatc | 1920 |
| cgtaacccgc aagttgatgg ctatctggcc gtctgggttc cggtaggtgc gtcggagaat | 1980 |
| caggatgttc gtgtggcgcc gagcaaagag aagaacagct ccggtctggt ttacgagagc | 2040 |
| aatgctgccc tggatagcca agttatctac gaaggcttca gcaacttcca ggacttcgtt | 2100 |
| cagaatccga ccagtatac caacaaaaag attgcagaga atgcaaattt gttcaaatcc | 2160 |
| tggggtatta ccagctttga atttgcgccg cagtacgtga gctcggatga tggtagcttc | 2220 |
| ctggacagcg ttattcagaa cggttatgcg tttacggacc gctacgacat tggtatgagc | 2280 |
| aaagacaaca aatatggttc gctggcggat ttgaaggcag cactgaagag cttgcatgcc | 2340 |
| gttggtatta gcgcaatcgc ggattgggtt cctgatcaga tctacaatct gccaggcgac | 2400 |
| gaggtcgtca ccgcaacccg cgttaacaac tacggcgaaa ccaaagatgg tgcaatcatt | 2460 |
| gatcactctt tgtacgcggc caaaacccgt acttttggta acgactacca gggtaagtat | 2520 |
| ggtggtgcgt tcctggacga gctgaaacgt ctgtatccgc agatctttga ccgcgttcag | 2580 |
| atttctaccg gtaagcgcat gaccacggac gagaagatca cccaatggtc tgcaaagtat | 2640 |
| atgaacggta cgaacatctt ggaccgtggc tctgaatacg ttttgaagaa tggtctgaat | 2700 |
| ggttactatg gcaccaatgg tggcaaagtt tcgctgccga agttgtggg tagcaatcaa | 2760 |
| agcacgaatg gcgacaatca aaacggcgac ggtagcggca gtttgaaaa gcgtctgttc | 2820 |
| agcgtgcgtt accgttataa caatggccag tacgcgaaaa atgcctttat caaagataac | 2880 |
| gacggcaatg tttactattt cgacaatagc ggtcgtatgg ctgtcggtga gaaaacgatt | 2940 |
| gacggcaagc agtacttctt cctggctaat ggcgttcagc tgcgtgacgg ctaccgtcaa | 3000 |
| aatcgtcgcg gtcaggtgtt ttactacgac cagaatggtg tgctgaacgc aaacggtaaa | 3060 |

-continued

```
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg tgcaattcg ctactatgac gcgaatagcg gtgagatggc acgcaatcgt     3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tgcaacctg cgctattacg acgttaacag cggtgagctg     3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                           3744
```

<210> SEQ ID NO 10
<211> LENGTH: 1247
<212> TYPE: PRT
<213> ORGANISM: Streptococcus salivarius

<400> SEQUENCE: 10

```
Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
                20                  25                  30

Ser Gln Tyr Phe Asn Ala Glu Thr Gly Glu Leu Ser Asn Gln Lys Glu
            35                  40                  45

Tyr Arg Phe Asp Lys Asn Gly Gly Thr Gly Ser Ser Ala Asp Ser Thr
        50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Pro Ser
        115                 120                 125

Lys Ala Ile Gln Ala Ser Tyr Leu Asn Tyr Met Lys Glu Gln Gly Leu
130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Ile Lys Asn Phe Val Lys
            180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
    210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
```

```
                       245                 250                 255
Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
        275                 280                 285

Ile Thr Gly Gly Ser Glu Asp Glu Asn Phe Asp Gly Val Arg Val Asp
    290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
    370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
        515                 520                 525

Ile Gly Tyr Gly Asn Thr Asn Gly Trp Asp Ala Ala Gly Val Leu Thr
    530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
            580                 585                 590

Arg Asn Gln Ala Tyr Arg Pro Leu Leu Leu Thr Thr Asn Asp Gly Val
        595                 600                 605

Ala Thr Tyr Leu Asn Asp Ser Asp Ala Asn Gly Ile Val Lys Tyr Thr
    610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670
```

```
Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
                740                 745                 750

Asp Arg Tyr Asp Ile Gly Met Ser Lys Asp Asn Lys Tyr Gly Ser Leu
                755                 760                 765

Ala Asp Leu Lys Ala Ala Leu Lys Ser Leu His Ala Val Gly Ile Ser
            770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                    805                 810                 815

Gly Ala Ile Ile Asp His Ser Leu Tyr Ala Ala Lys Thr Arg Thr Phe
                820                 825                 830

Gly Asn Asp Tyr Gln Gly Lys Tyr Gly Gly Ala Phe Leu Asp Glu Leu
            835                 840                 845

Lys Arg Leu Tyr Pro Gln Ile Phe Asp Arg Val Gln Ile Ser Thr Gly
850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                885                 890                 895

Asn Gly Leu Asn Gly Tyr Tyr Gly Thr Asn Gly Gly Lys Val Ser Leu
                900                 905                 910

Pro Lys Val Val Gly Ser Asn Gln Ser Thr Asn Gly Asp Asn Gln Asn
            915                 920                 925

Gly Asp Gly Ser Gly Lys Phe Glu Lys Arg Leu Phe Ser Val Arg Tyr
930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln Val Phe Tyr
            995                 1000                1005

Tyr Asp Gln Asn Gly Val Leu Asn Ala Asn Gly Lys Gln Asp Pro
    1010                1015                1020

Lys Pro Asp Asn Asn Asn Ala Ser Gly Arg Asn Gln Phe Val
    1025                1030                1035

Gln Ile Gly Asn Asn Val Trp Ala Tyr Tyr Asp Gly Asn Gly Lys
    1040                1045                1050

Arg Val Thr Gly His Gln Asn Ile Asn Gly Gln Glu Leu Phe Phe
    1055                1060                1065

Asp Asn Asn Gly Val Gln Val Lys Gly Arg Thr Val Asn Glu Asn
    1070                1075                1080
```

-continued

```
Gly Ala Ile Arg Tyr Tyr Asp Ala Asn Ser Gly Glu Met Ala Arg
    1085            1090                1095

Asn Arg Phe Ala Glu Ile Glu Pro Gly Val Trp Ala Tyr Phe Asn
    1100            1105                1110

Asn Asp Gly Thr Ala Val Lys Gly Ser Gln Asn Ile Asn Gly Gln
    1115            1120                1125

Asp Leu Tyr Phe Asp Gln Asn Gly Arg Gln Val Lys Gly Ala Leu
    1130            1135                1140

Ala Asn Val Asp Gly Asn Leu Arg Tyr Tyr Asp Val Asn Ser Gly
    1145            1150                1155

Glu Leu Tyr Arg Asn Arg Phe His Glu Ile Asp Gly Ser Trp Tyr
    1160            1165                1170

Tyr Phe Asp Gly Asn Gly Asn Ala Val Lys Gly Met Val Asn Ile
    1175            1180                1185

Asn Gly Gln Asn Leu Leu Phe Asp Asn Asn Gly Lys Gln Ile Lys
    1190            1195                1200

Gly His Leu Val Arg Val Asn Gly Val Val Arg Tyr Phe Asp Pro
    1205            1210                1215

Asn Ser Gly Glu Met Ala Val Asn Arg Trp Val Glu Val Ser Pro
    1220            1225                1230

Gly Trp Trp Val Tyr Phe Asp Gly Glu Gly Arg Gly Gln Ile
    1235            1240                1245
```